(12) United States Patent
Mark

(10) Patent No.: US 8,702,738 B2
(45) Date of Patent: Apr. 22, 2014

(54) TISSUE REMOVAL DEVICE FOR NEUROSURGICAL AND SPINAL SURGERY APPLICATIONS

(75) Inventor: Joseph L. Mark, Indianapolis, IN (US)

(73) Assignee: Nico Corporation, Indianapolis, IN (US)

( * ) Notice: Subject to any disclaimer, the term of this patent is extended or adjusted under 35 U.S.C. 154(b) by 818 days.

(21) Appl. No.: 12/391,579

(22) Filed: Feb. 24, 2009

(65) Prior Publication Data

US 2010/0152760 A1 Jun. 17, 2010

Related U.S. Application Data

(63) Continuation-in-part of application No. 12/389,447, filed on Feb. 20, 2009, which is a continuation-in-part of application No. 12/336,054, filed on Dec. 16, 2008, and a continuation-in-part of application No. 12/336,086, filed on Dec. 16, 2008.

(51) Int. Cl.
*A61B 17/32* (2006.01)

(52) U.S. Cl.
USPC .......................................... 606/177; 606/167

(58) Field of Classification Search
USPC .......................................... 606/180, 167, 177
See application file for complete search history.

(56) References Cited

U.S. PATENT DOCUMENTS

| | | | |
|---|---|---|---|
| 2,044,823 A | 6/1936 | Whiteside | |
| D161,178 S * | 12/1950 | Waldron | D6/303 |
| 4,071,029 A | 1/1978 | Richmond et al. | |
| 4,210,146 A | 7/1980 | Banko | |
| 4,493,698 A | 1/1985 | Wang et al. | |
| 4,650,460 A | 3/1987 | Roizenblatt | |
| 4,770,654 A | 9/1988 | Rogers et al. | |
| 4,940,061 A | 7/1990 | Terwilliger et al. | |
| 5,085,658 A * | 2/1992 | Meyer | 606/46 |
| 5,098,426 A | 3/1992 | Sklar et al. | |
| 5,195,541 A | 3/1993 | Obenchain | |
| 5,403,276 A | 4/1995 | Schechter et al. | |
| 5,411,513 A | 5/1995 | Ireland et al. | |

(Continued)

FOREIGN PATENT DOCUMENTS

| | | |
|---|---|---|
| AU | 2011253790 A1 | 1/2012 |
| EP | 0 125 070 A2 | 11/1984 |

(Continued)

OTHER PUBLICATIONS

PCT International Search Reported for PCT/US2009/068225 dated Oct. 4, 2010.

(Continued)

*Primary Examiner* — Max Hindenburg
*Assistant Examiner* — Renee Danega
(74) *Attorney, Agent, or Firm* — Kristin L. Murphy; Brooks Kushman P.C.

(57) ABSTRACT

A tissue cutting device that is especially suited for neurosurgical applications is disclosed and described. The device includes a handpiece and an outer cannula in which a reciprocating inner cannula is disposed. The inner cannula includes a hinge between a body section and a cutting section that allows the cutting section to pivot when the inner cannula reciprocates within the outer cannula. A tissue collector is also provided and is in fluid communication with the lumen of the inner cannula. The handpiece includes a proximal section that is angled with respect to a distal section.

38 Claims, 23 Drawing Sheets

(56) References Cited

U.S. PATENT DOCUMENTS

| | | | |
|---|---|---|---|
| 5,415,169 A | 5/1995 | Siczek et al. | |
| 5,456,689 A | 10/1995 | Kresch et al. | |
| 5,643,304 A | 7/1997 | Schechter et al. | |
| 5,772,627 A | 6/1998 | Acosta et al. | |
| 5,782,849 A | 7/1998 | Miller | |
| 5,810,744 A | 9/1998 | Chu et al. | |
| 5,911,701 A | 6/1999 | Miller et al. | |
| 5,916,231 A | 6/1999 | Bays | |
| 5,997,560 A | 12/1999 | Miller | |
| 6,017,354 A | 1/2000 | Culp et al. | |
| 6,032,673 A | 3/2000 | Savage et al. | |
| 6,086,544 A | 7/2000 | Hibner et al. | |
| 6,152,871 A | 11/2000 | Foley et al. | |
| 6,179,829 B1 | 1/2001 | Bisch et al. | |
| 6,245,084 B1 | 6/2001 | Mark et al. | |
| 6,269,888 B1 * | 8/2001 | Schuda et al. | 173/48 |
| 6,312,441 B1 | 11/2001 | Deng | |
| 6,322,549 B1 | 11/2001 | Eggers et al. | |
| 6,402,701 B1 | 6/2002 | Kaplan et al. | |
| 6,419,641 B1 | 7/2002 | Mark et al. | |
| 6,491,699 B1 | 12/2002 | Henderson et al. | |
| 6,592,530 B1 | 7/2003 | Farhadi | |
| 6,609,020 B2 | 8/2003 | Gill | |
| D479,455 S | 9/2003 | Waldron | |
| 6,629,986 B1 | 10/2003 | Ross et al. | |
| 6,659,998 B2 | 12/2003 | DeHoogh et al. | |
| 7,019,234 B1 | 3/2006 | Mezhinsky et al. | |
| 7,481,775 B2 | 1/2009 | Weikel, Jr. et al. | |
| 7,678,552 B2 | 3/2010 | Kornblith | |
| 2001/0037114 A1 | 11/2001 | Dinger et al. | |
| 2002/0103496 A1 | 8/2002 | Harper et al. | |
| 2003/0045811 A1 | 3/2003 | Hinchliffe et al. | |
| 2003/0047434 A1 | 3/2003 | Hanson et al. | |
| 2003/0073980 A1 | 4/2003 | Finlay et al. | |
| 2004/0049217 A1 * | 3/2004 | Ross et al. | 606/171 |
| 2005/0027210 A1 | 2/2005 | Miller | |
| 2005/0085798 A1 | 4/2005 | Hofmann et al. | |
| 2005/0103607 A1 | 5/2005 | Mezhinsky | |
| 2005/0154407 A1 | 7/2005 | Simpson | |
| 2005/0277970 A1 | 12/2005 | Norman et al. | |
| 2006/0241343 A1 | 10/2006 | Miller et al. | |
| 2007/0073226 A1 | 3/2007 | Polidoro et al. | |
| 2007/0073326 A1 * | 3/2007 | Miller et al. | 606/180 |
| 2007/0149977 A1 | 6/2007 | Heavener | |
| 2008/0114387 A1 | 5/2008 | Hertweck et al. | |
| 2008/0234720 A1 | 9/2008 | Chang et al. | |
| 2008/0243105 A1 | 10/2008 | Horvath | |
| 2008/0249366 A1 | 10/2008 | Gruber et al. | |
| 2008/0249553 A1 | 10/2008 | Gruber et al. | |
| 2008/0262476 A1 | 10/2008 | Krause et al. | |
| 2009/0124975 A1 | 5/2009 | Oliver et al. | |
| 2009/0131819 A1 | 5/2009 | Ritchie et al. | |
| 2009/0281477 A1 | 11/2009 | Mikus et al. | |
| 2010/0292607 A1 | 11/2010 | Moore et al. | |

FOREIGN PATENT DOCUMENTS

| | | | |
|---|---|---|---|
| EP | 0497520 A1 | 8/1992 | |
| EP | 1201210 A1 | 5/2002 | |
| EP | 1 714 617 A1 | 10/2006 | |
| EP | 1815798 A2 | 8/2007 | |
| EP | 1859742 A1 | 11/2007 | |
| WO | WO 94/18894 | * | 9/1994 |
| WO | WO-94/18894 A1 | 9/1994 | |
| WO | WO-9613845 A1 | 5/1996 | |
| WO | WO-98/46147 A1 | 10/1998 | |
| WO | WO-00/22994 A1 | 4/2000 | |
| WO | WO-0230303 A1 | 4/2002 | |
| WO | WO-03045290 A1 | 6/2003 | |
| WO | WO-2006/123312 A1 | 11/2006 | |
| WO | WO-2007002230 A1 | 1/2007 | |
| WO | WO-2007005507 A2 | 1/2007 | |
| WO | WO-2007047380 A2 | 4/2007 | |
| WO | WO-2007062412 A2 | 5/2007 | |
| WO | WO-2008/058157 A2 | 5/2008 | |

OTHER PUBLICATIONS

Publication entitled "Extending Your Arthroscopic Reach", published by Smith&Nephew Dyonics, Inc., Feb. 1992.

Publication entitled: "EndoFlex Steerable Nucelotome for Endoscopic Microdisectomy", published by Surgical Dynamics, 1993.

Publication entitled: "Nucleotome Flex II for Automated Percuaneous Lumbar Discectomy", published by Surgical Dynamics, 1992.

Publication entitled: "Surgical Technique Nucelotome Micro I for Automated Open Lumbar Discectomy", published by Surgical Dynamics, 1992.

Publication entitled; "Micro II Bendable Nucelotome for Open Lumbar Discectomy", published by Surgical Dynamics, 1993.

Publication entitled, "The World's Thinnest, Smallest & Strongest Heat Shrink Tubing", published by Advanced Polymers, Inc.

Publication entitled, "Positron Emission Tomography-Guided Volumetric Resection of Supratentorial High-Grade Glimoas: A Survival Analysis in 66 Consecutive Patients" by Benoit J.M. Pirotte, M.D., Ph.D. et al.—Published in Clinical Studies Neurosurgery, vol. 64, No. 3, Mar. 2009.

Publication entitled, "Hemostatic Agents, Sealants, and Tissue Adhesives", authored by Arthur Hill, M.D. and Ming Si, M.D.; publisher, University of California, San Francisco.

Publication entitled, "New Device Approval—Arista™ AH Absorbable Hemostat—P050038", Published in FDA U.S. Food and Drug Administaration, dated Apr. 13, 2009.

Publication entitled: "Prescision Begins with a Linemaster Switch", published by Linesmaster Switch Corp., 2000.

PCT International Search Report for PCT/US2009/068313 dated Mar. 11, 2010.

Annex to Form PCT/ISA/206 Communication Relating to the Results of the Partial International Search for PCT/US2009/068329 dated Mar. 5, 2010.

Non-Final Office action dated Sep. 29, 2011 for U.S. Appl. No. 12/336,054.

D. M. Keller, PhD, "Patients With Newly Diangosed Glioblastoma Benefit Even From Less Than Total Resection," http://www.medscape.com/viewarticle/721786; (May 13, 2010).

Non-Final Office Action dated Oct. 6, 2011 for U.S. Appl. No. 12/336,086.

Non-Final Office Action dated Oct. 6, 2011 for U.S. Appl. No. 12/389,447.

Non-Final Office Action dated Oct. 6, 2011 for U.S. Appl. No. 12/404,407.

Non-Final Office Aciton dated Oct. 13, 2011 for U.S. Appl. No. 12/481,219.

Non-Final Office Action dated Oct. 13, 2011 for U.S. Appl. No. 12/391,579.

PCT International Search Report dated Aug. 3, 2011 for PCT/US2011/037092.

PCT International Search Report dated Sep. 23, 2011 for PCT/US2009/068329.

U.S. Appl. No. 12/336,054, filed Dec. 16, 2008.
U.S. Appl. No. 12/336,086, filed Dec. 16, 2008.
U.S. Appl. No. 12/389,447, filed Feb. 20, 2009.
U.S. Appl. No. 12/404,407, filed Mar. 16, 2009.
U.S. Appl. No. 12/435,724, filed May 5, 2009.
U.S. Appl. No. 12/475,258, filed May 29, 2009.
U.S. Appl. No. 12/481,219, filed Jun. 9, 2009.
U.S. Appl. No. 12/782,879, filed May 19, 2010.
U.S. Appl. No. 13/269,339, filed Oct. 7, 2011.
U.S. Appl. No. 13/296,745, filed Nov. 15, 2011.
U.S. Appl. No. 13/352,069, filed Jan. 17, 2012.

Non-Final Office Action dated Oct. 5, 2012 for U.S. Appl. No. 12/481,219.

Final Office Action dated Oct. 16, 2012 for U.S. Appl. No. 12/435,724.

(56) References Cited

OTHER PUBLICATIONS

Response to Final Office Action dated Oct. 16, 2012 for U.S. Appl. No. 12/435,724.
Response to Final Office Action dated Sep. 25, 2012 for U.S. Appl. No. 12/404,407.
Notice of Allowance dated Jan. 16, 2013 for U.S. Appl. No. 12/336,054.
Notice of Allowance dated Feb. 11, 2013 for U.S. Appl. No. 12/435,724.
Final Office Action dated Apr. 24, 2012 for U.S. Appl. No. 12/481,219.
Final Office Action dated May 1, 2012 for U.S. Appl. No. 12/389,447.
Response to Non-Final Office Action dated Jan. 11, 2012 for U.S. Appl. No. 12/475,258.
Response to Non-Final Office Action dated Jan. 6, 2012 for U.S. Appl. No. 12/435,724.
Final Office Action dated May 22, 2012 for U.S. Appl. No. 12/475,258.
Response to Non-Final Office Action dated Jan. 27, 2012 for U.S. Appl. No. 12/782,879.
Final Office Action dated May 15, 2012 for U.S. Appl. No. 12/336,054.
Final Office Action dated Jul. 27, 2012 for U.S. Appl. No. 12/435,724.
Response to Non-Final Office Action dated Mar. 8, 2012 for U.S. Appl. No. 12/404,407.
Response to Final Office Action dated Apr. 24, 2012 for U.S. Appl. No. 12/481,219.
Response to Final Office Action dated May 15, 2012 for U.S. Appl. No. 12/336,054.
Response to Final Office Action dated Jul. 27, 2012 for U.S. Appl. No. 12/435,724.
Final Office Action dated Sep. 25, 2012 for U.S. Appl. No. 12/404,407.
Response to Final Office Action dated May 22, 2012 for U.S. Appl. No. 12/475,258.
Response to Final Office Action dated May 1, 2012 for U.S. Appl. No. 12/389,447.
Notice of Allowance dated Oct. 2, 2012 for U.S. Appl. No. 12/782,879.
Publication entitled "Heavy Duty Foot Potentionmeter", published at www.herga.com, Herga Electric Ltd. Apr. 30, 2009.
Publication entitled: "Vacuum Generators, How the E-Vac Works", published in Exair Corporation, Copyright 2009.
Publication entitled: "An Automated Tumor Resection Device for Neurological Surgery," authors, Martin L. Lazar, M.D., et al; pushed by Texas Neurological Institute at Dallas, (vol. 3, No. 3 1978).
Publication entitled, "Automated Tumor Extraction Device for Neurological Surgery," by Wang et al.; published by Journal of Clinical Engineer/Apr.-Jun. 1979.
Non-Final Office Action dated Jan. 27, 2012 for U.S. Appl. No. 12/782,879.
Response to Non-Final Office Action dated Oct. 6, 2011 for U.S. Appl. No. 12/336,086.
Response to Non-Final Office Action dated Oct. 13, 2011 for U.S. Appl. No. 12/481,219.
Response to Non-Final Office Action dated Oct. 6, 2011 for U.S. Appl. No. 12/389,447.
Non-Final Office Action dated Mar. 8, 2012 for U.S. Appl. No. 12/404,407.
Response to Non-Final Office Action dated Sep. 29, 2011 for U.S. Appl. No. 12/336,054.

* cited by examiner

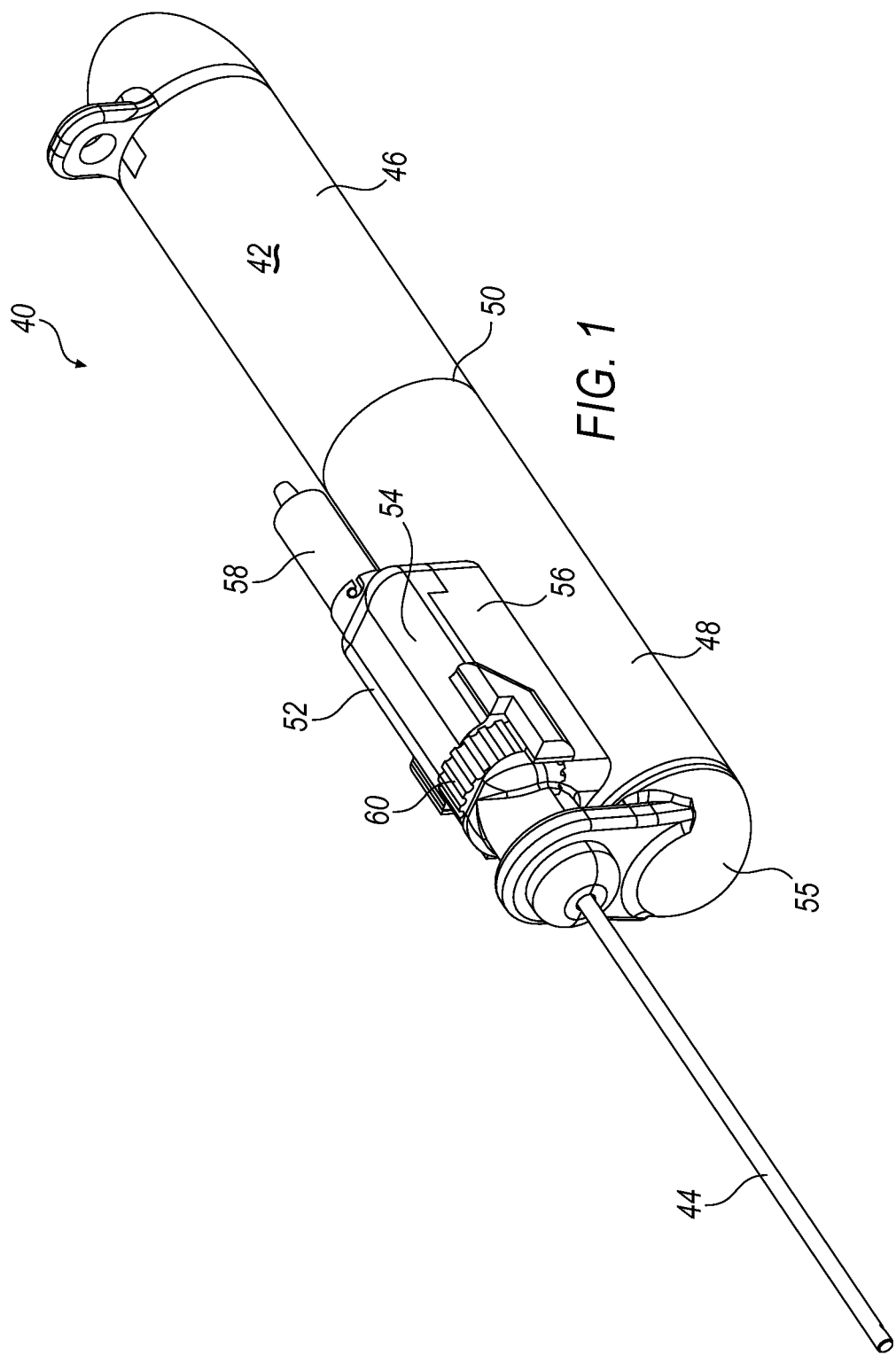

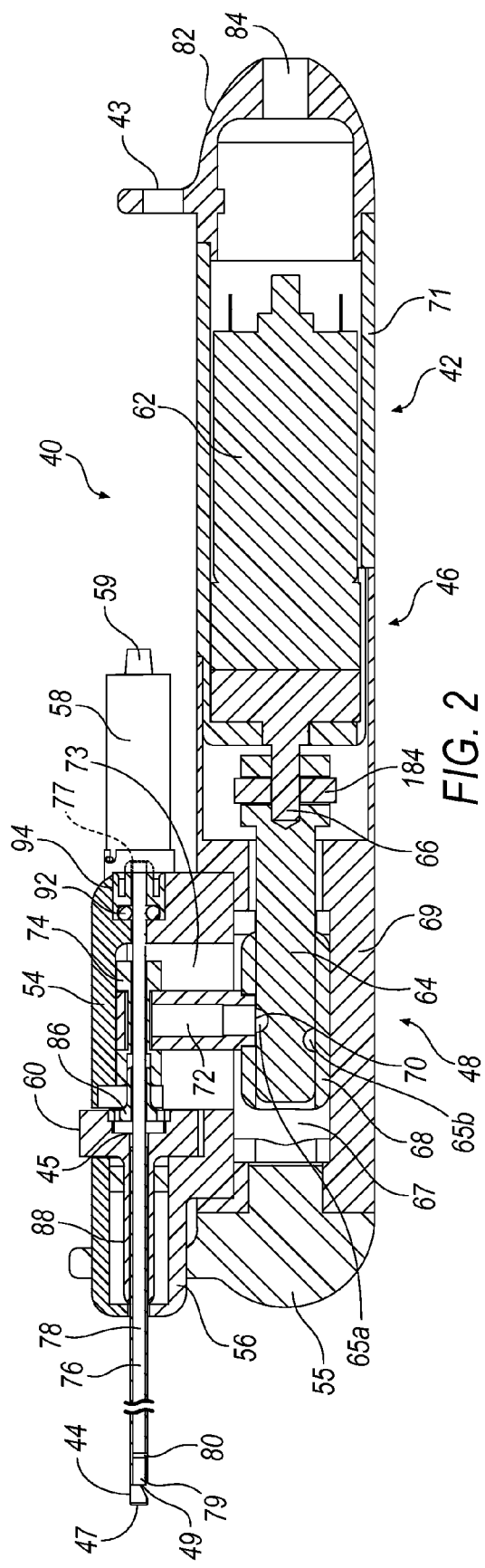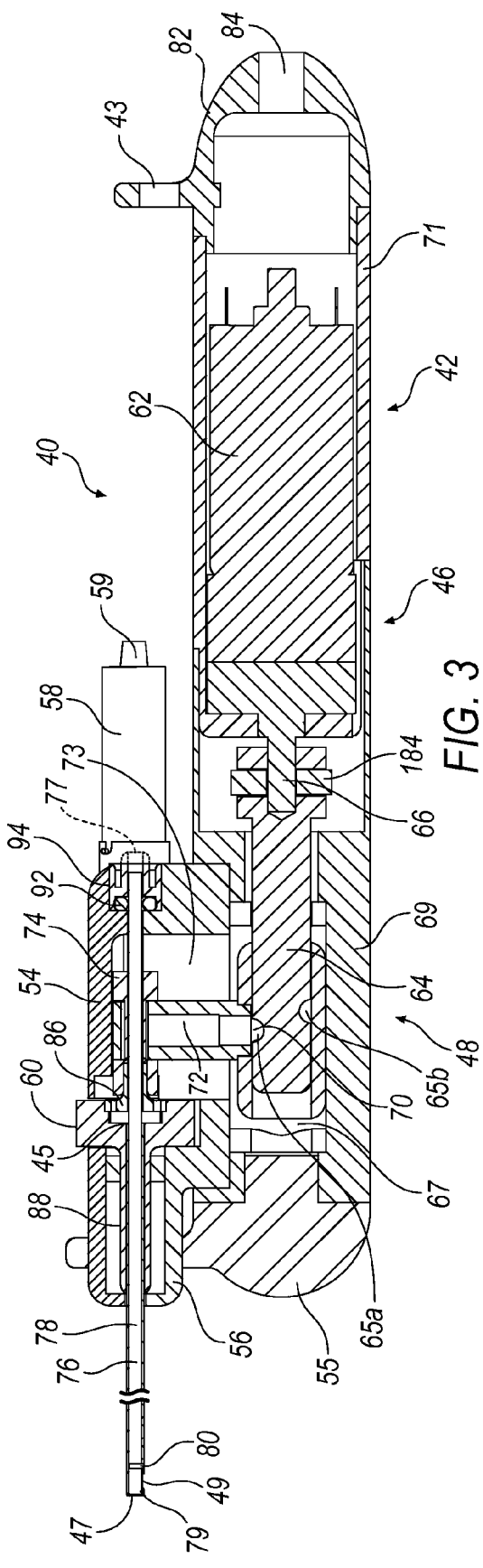

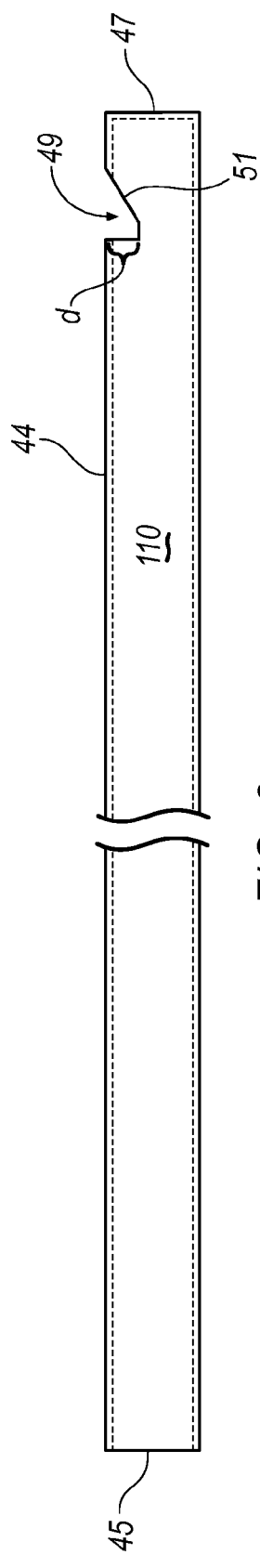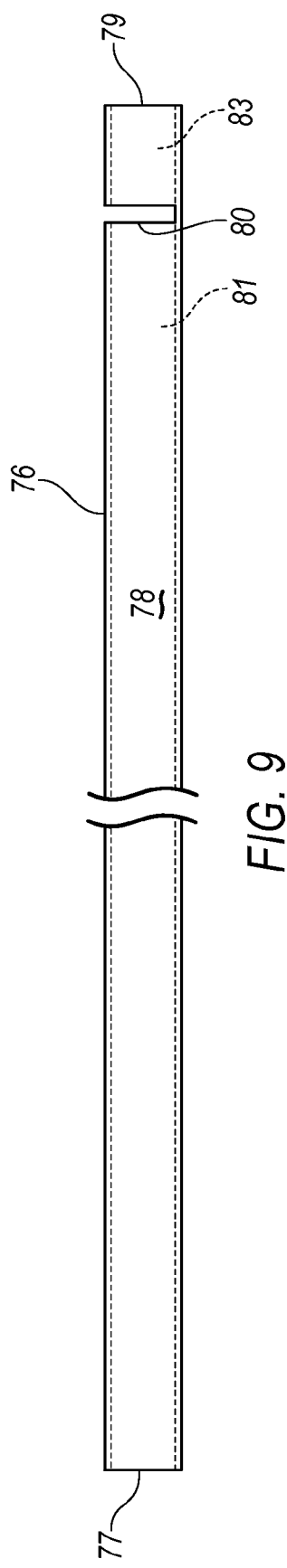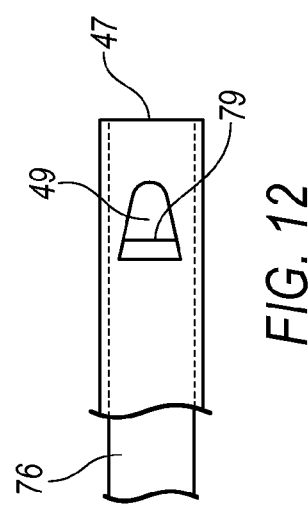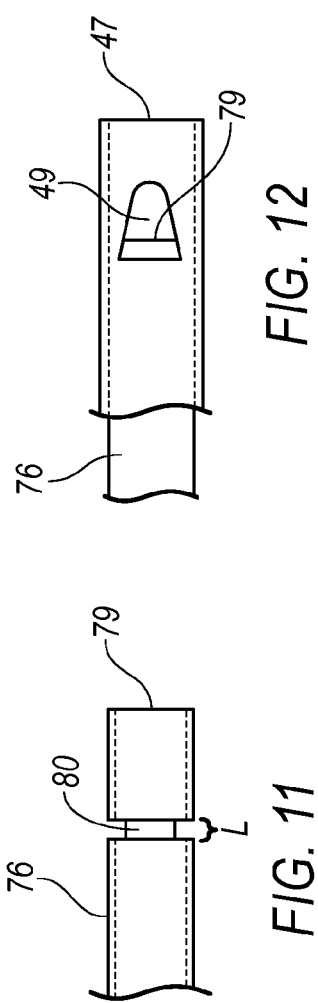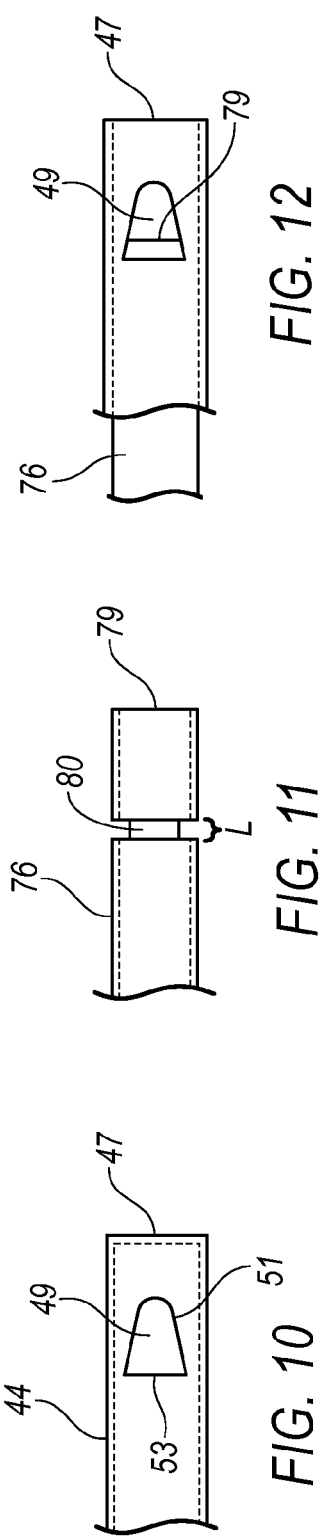

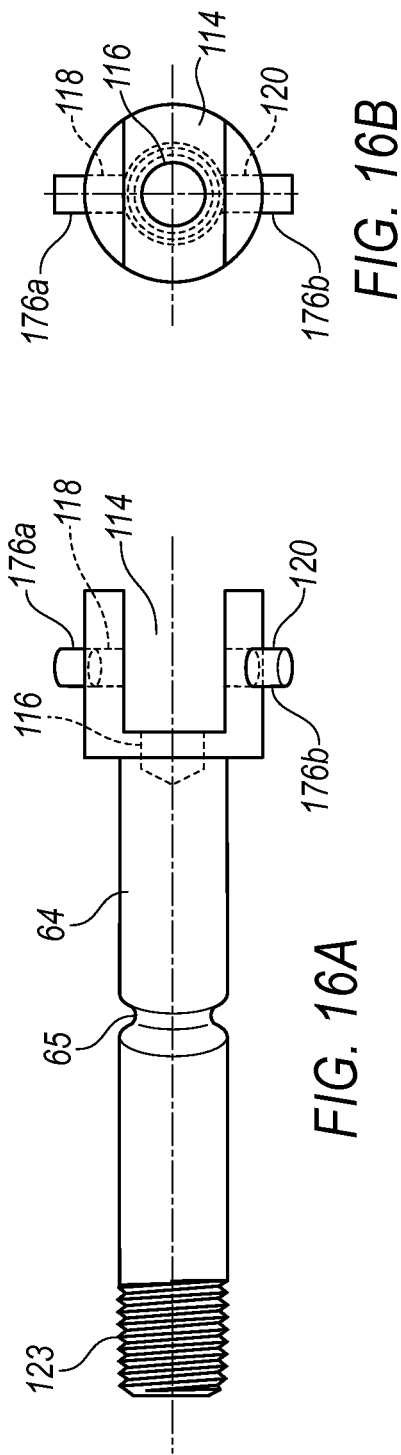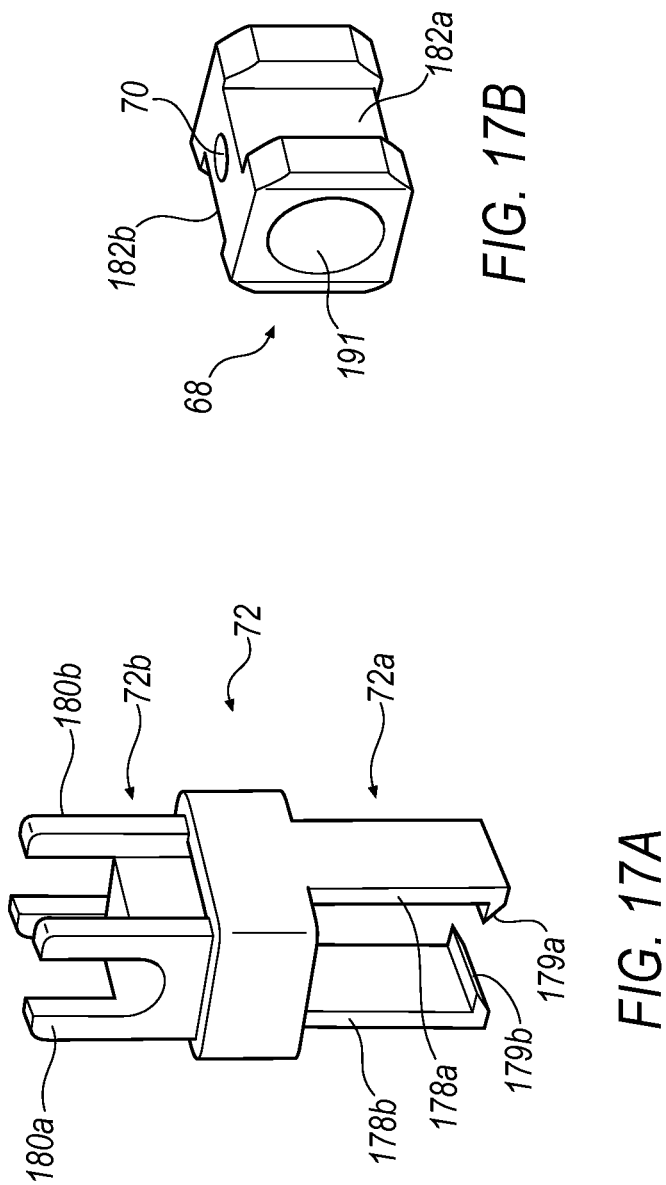

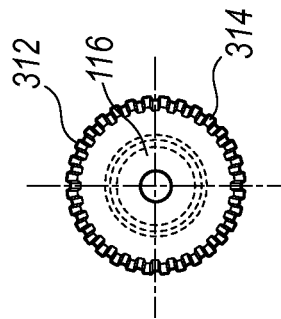
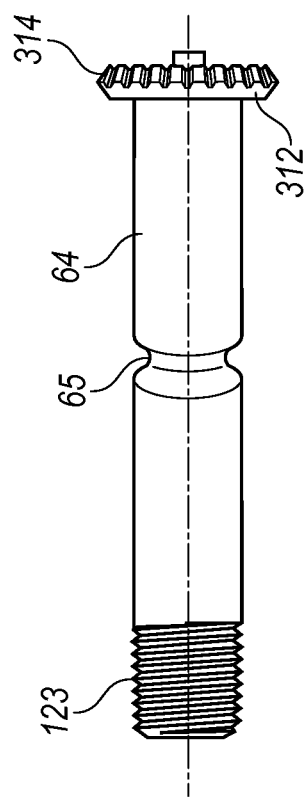
FIG. 32B
FIG. 32A

TISSUE REMOVAL DEVICE FOR NEUROSURGICAL AND SPINAL SURGERY APPLICATIONS

RELATED APPLICATIONS

This application is a continuation-in-part of U.S. application Ser. No. 12/389,447, filed Feb. 20, 2009, which claims the benefit of U.S. application Ser. No. 12/336,054, filed Dec. 16, 2008 and U.S. application Ser. No. 12/336,086, filed Dec. 16, 2008, each of which is hereby incorporated by reference in its entirety.

TECHNICAL FIELD

The present disclosure relates to tissue cutting devices, in particular, tissue cutting devices that are suited for neurosurgical and spinal surgical procedures.

BACKGROUND

Various abnormalities of the neurological system, such as brain and spinal tumors, cysts, lesions, or neural hematomas, can cause severe health risks to patients afflicted by them, including deterioration in motor skills, nausea or vomiting, memory or communication problems, behavioral changes, headaches, or seizures. In certain cases, resection of abnormal tissue masses is required. However, given the complexity and importance of the neurological system, such neurosurgical procedures are extremely delicate and must be executed with great precision and care. Many known tissue cutting devices suffer from an inability to quickly and cleanly sever neurological tissue samples without causing "traction" or pull on the surrounding tissue. In addition, many known devices are not configured to both "debulk" large structures and to finely shave smaller, more delicate structures and lack the flexibility needed in many procedures. Furthermore, many neurological procedures impose significant space limitations on the surgeon, and the tissue resection device needs to be manipulable by the surgeon with one hand in relatively small spaces. Many known devices either emulsify the resected tissue, macerate the resected tissue, or thermally damage the tissue rendering it unsuitable for subsequent analysis (e.g., pathologic and/or histologic analysis) which is necessary for the determination of the most effective post resection treatment therapies. Thus, a need has arisen for a tissue cutting device that addresses the foregoing issues.

BRIEF DESCRIPTION OF THE DRAWINGS

Embodiments of the present disclosure will now be described by way of example in greater detail with reference to the attached figures, in which:

FIG. 1 is a perspective view of a tissue cutting device in accordance with a first embodiment;

FIG. 2 is a cross-sectional view of the tissue cutting device of FIG. 1 depicting an inner cannula in a first relative position with respect to an outer cannula in which the inner cannula's distal end is located proximally of the outer cannula's distal end;

FIG. 3 is a cross-sectional view of the tissue cutting device of FIG. 1 depicting the inner cannula in a second relative position with respect to the outer cannula in which the inner cannula's distal end is located at the distal end of the outer cannula;

FIG. 8 is a broken side elevation view of the outer cannula of the tissue cutting device of FIG. 1;

FIG. 9 is a broken side elevation view of the inner cannula of the tissue cutting device of FIG. 1;

FIG. 10 is a top plan view of a portion of the outer cannula of the tissue cutting device of FIG. 1 with the inner cannula removed from the outer cannula;

FIG. 11 is a top plan view of a portion of the inner cannula of the tissue cutting device of FIG. 1;

FIG. 12 is a top plan view of a portion of the outer cannula and inner cannula of FIG. 1 depicting the inner cannula inserted into the outer cannula;

FIG. 16a is a side elevation view of a cam of the tissue cutting device of FIG. 1;

FIG. 16b is an end elevation view of the cam of FIG. 16a;

FIG. 17a is a perspective view of a cam transfer mechanism of the tissue cutting device of FIG. 1;

FIG. 17b is a perspective view of a cam follower of the tissue cutting device of FIG. 1;

FIG. 32a is a side elevation view of a cam of the tissue cutting device of FIG. 28;

FIG. 32b is an end elevation view of the cam of FIG. 32a;

DETAILED DESCRIPTION

Figure 4:
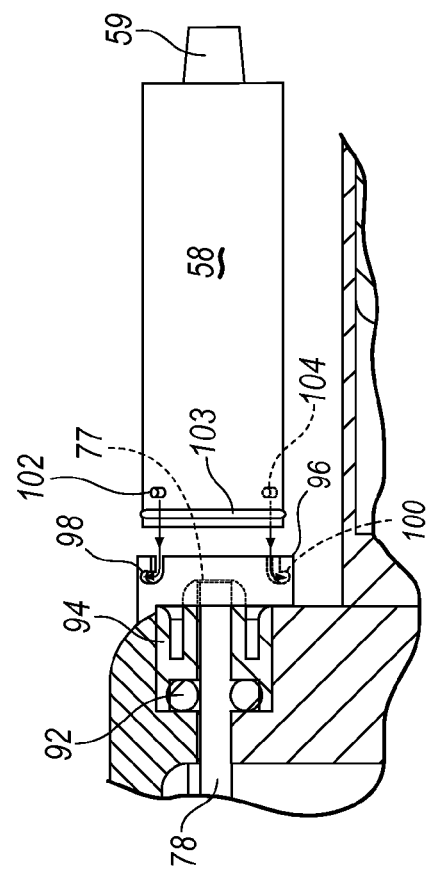
FIG. 4 is a partial cross-sectional view of the tissue cutting device of FIG. 1 in a first configuration in which a device-mounted tissue collector is disconnected from a tissue cutting device housing.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are tissue cutting devices that are suited for neurosurgical applications such as the removal of spine and brain tissue. The devices include a handpiece that is grippable with a single hand and an inner cutting cannula that reciprocates within an outer cannula. The inner and outer cannulae are offset from the handpiece to provide surgeons with an enhanced ability to perform various neurosurgical procedures. Referring to FIG. 1, a tissue cutting device 40 includes a handpiece 42 and an outer cannula 44. In one exemplary configuration, handpiece 42 is generally cylindrical in shape and is preferably sized and shaped to be grasped with a single hand. Handpiece 42 includes a lower housing 50 which comprises a proximal section 46 and distal section 48. Lower housing 50 comprises a proximal-most housing portion 82 (FIGS. 2 and 3) that is connected to a motor housing 71, and a cam housing 69 that is connected to motor housing 71. A front housing section 55 is connected to cam housing 69. Upper housing 52 is also provided. A tissue collector 58 may be operatively connected to upper housing 52 (as will be explained in further detail below). A rotation dial 60 for rotating the outer cannula 44 with respect to handpiece 42 is also mounted to upper housing 52.

Figure 20:
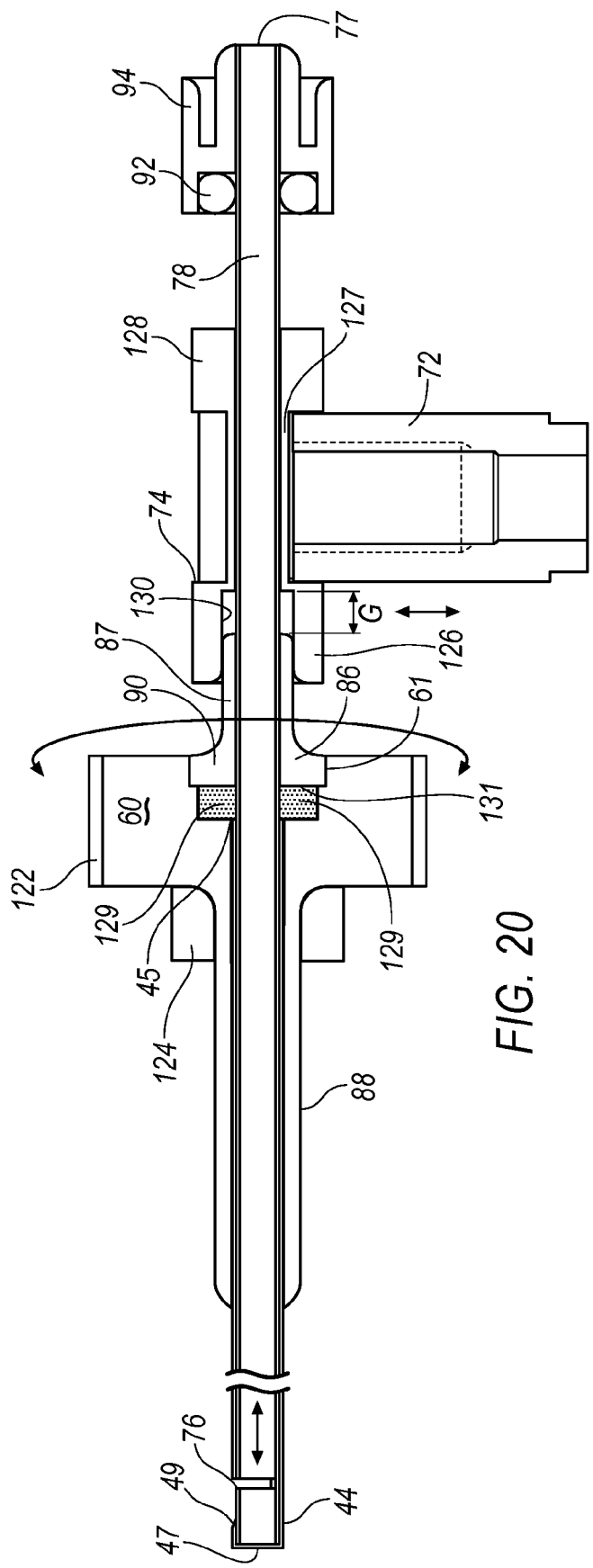
FIG. 20 is a side elevation view of an inner and outer cannula assembly of the tissue cutting device of FIG. 1.

As best seen in FIGS. 2, 3, and 20, outer cannula 44 includes an open proximal end 45, a closed distal end 47, and a distal opening 49 proximate distal end 47. Tissue cutting device 40 further comprises an inner cannula 76 which is partially disposed in an outer cannula lumen 110. Inner cannula 76 is configured to reciprocate within outer cannula lumen 110 and to cut tissue samples entering outer cannula 44 via outer cannula distal opening 49, as will be described in greater detail below. Inner cannula 76 reciprocates between a proximal position, which is depicted in FIG. 2 and a distal position which is depicted in FIG. 3. Inner cannula 76 includes an open proximal end 77 and an open distal end 79. Distal end 79 is preferably configured to cut tissue, and in preferred embodiments is capable of cutting neurological system tissues such as those from the brain or spine. In one exemplary embodiment, inner cannula distal end 79 is beveled in a radially inward direction to create a sharp circular tip and facilitate tissue cutting.

Outer cannula 44 is not translatable, and its position with respect to handpiece 42 along the direction of the longitudinal axis of handpiece 42 remains fixed. Motor 62 is disposed in proximal lower housing section 46 of handpiece 42 and is operably connected to inner cannula 76 to drive the reciprocation of inner cannula 76 within outer cannula lumen 110. Motor 62 may be a reciprocating or rotary motor. In addition, it may be electric or hydraulic. However, in the embodiment of FIGS. 2 and 3, motor 62 is a rotary motor, the rotation of which causes inner cannula 76 to reciprocate within outer cannula lumen 110.

Motor 62 is housed in motor housing 71, which defines a portion of lower housing proximal section 46. Motor 62 is connected to an inner cannula drive assembly 63 which is used to convert the rotational motion of motor 62 into the translational motion of inner cannula 76. At its proximal end, motor housing 71 is connected to proximal-most housing portion 82, which includes a power cable port 84 and a hose connector 43, which in the exemplary embodiment of FIG. 3 is an eyelet. Hose connector 43 provides a means of securely retaining a vacuum system hose to handpiece 42, thereby allowing vacuum to be supplied to tissue collector 58.

Inner cannula drive assembly 63 (not separately shown in figures) comprises a cam 64, a cam follower 68, a cam transfer 72, and a cannula transfer 74. Cam 64 is a generally cylindrical structure and is shown in detail in FIGS. 16A and 16B. A groove or channel 65 is defined in the surface of cam 64. In one exemplary embodiment, groove 65 is continuous and circumscribes the perimeter of cam 64 but is not oriented perpendicularly to the longitudinal axis of cam 64, i.e., groove 65 is angled with respect to the cam axis. Opposing points on groove 65 such as points 65a and 65b define pairs of "apexes" that are spaced apart along the longitudinal axis of the cam, i.e., the groove extends along a portion of the length of the cam. Cam 64 also includes a proximal opening 114

(FIG. 16a) for receiving a motor shaft and a proximal recess 116 into which a shaft may be snugly received. Holes 118 and 120 are provided for mounting position indicators that cooperate with a position sensor to determine the angular position of cam 64, and correspondingly, the linear position of inner cannula 76 within the outer cannula lumen 110, as discussed below.

Cam follower 68 is depicted in detail in FIG. 17B. Cam follower 68 is a generally rectangular block shaped structure with a hollow interior in which cam 64 is partially disposed. Cam follower 68 also includes a hole 70 in its upper face in which a ball bearing (not shown) is seated. The ball bearing rides in cam groove 65 and engages cam transfer 72. As a result, when cam 64 rotates, cam follower 68 translates along the length of handpiece 42. Cam follower 68 also includes lateral slots 182a and 182b that cooperatively engage corresponding members 178a, 178b from cam transfer 72.

Figure 15:
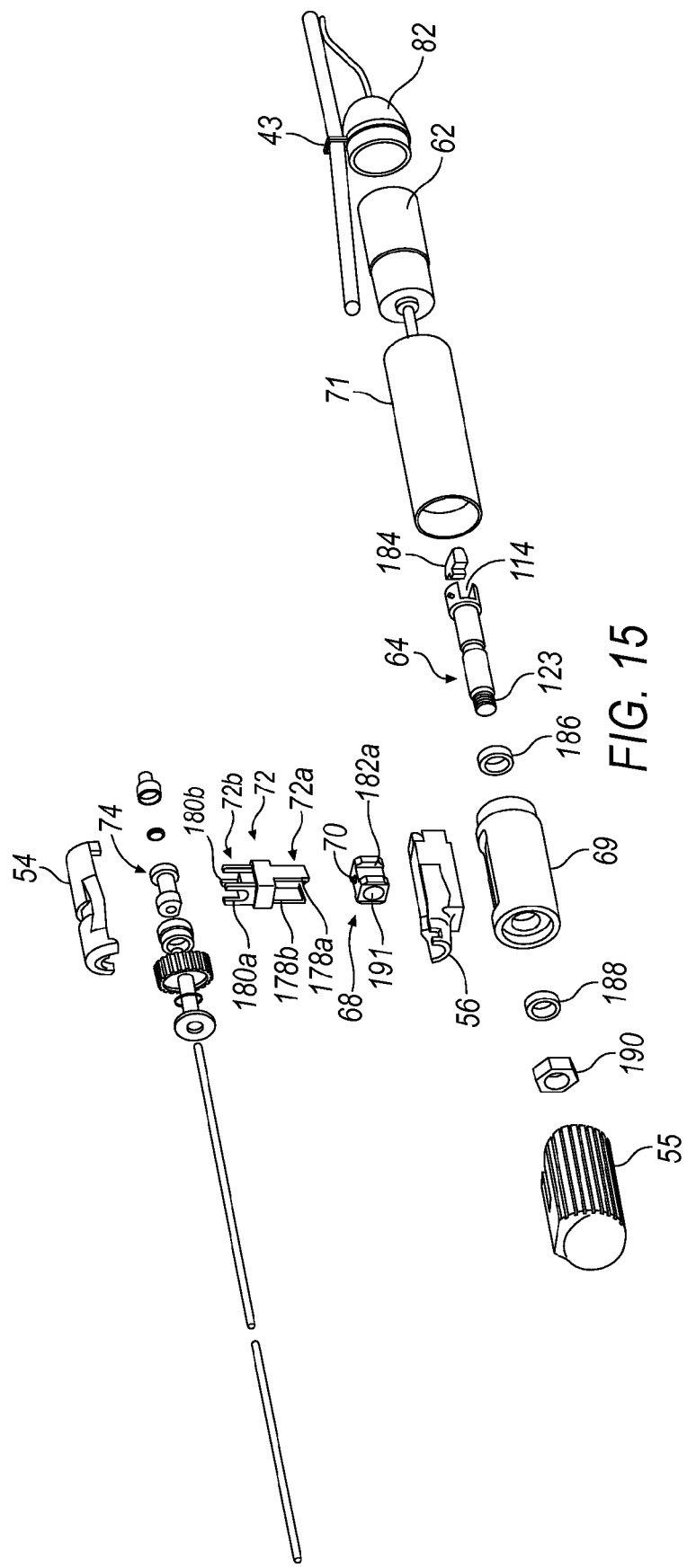
FIG. 15 is an exploded assembly view of the tissue cutting device of FIG. 1.

Cam follower 68 is disposed within a cam chamber 67 formed in cam housing 69. Cam 64 is partially disposed in cam chamber 67 and extends proximally therefrom to engage motor 62. Cam housing 69 comprises part of distal portion 48 of handpiece 42. Cam 64 does not reciprocate within cam chamber 67 and instead merely rotates about its own longitudinal axis. However, cam follower 68 reciprocates within cam chamber 67 along the direction of the length of handpiece 42. Cam follower 68 is open at its proximal end to receive cam 64. As shown in FIGS. 15 and 16A, cam 64 may optionally include a threaded distal end 123 that projects through a distal opening 191 (FIG. 17b) in cam follower 68 and which engages a nut 190 (FIG. 15) to prevent reciprocation of cam 64 relative to cam housing 69. Proximal cam bearing 186 and distal cam bearing 188 (FIG. 15) may also be provided to support cam 64 as it rotates within cam housing 69.

Cam transfer 72 extends from cam chamber 67 into a cam transfer chamber 73 formed in upper housing 52. As best seen in FIG. 17a, cam transfer 72 comprises a proximal end 72a that is attachable to cam follower 68 and a distal end 72b that is attachable to inner cannula 76 via cannula transfer 74. Proximal end 72a comprises a pair of spaced apart, downwardly extending members 178a and 178b, and distal end 72b comprises a pair of spaced apart upwardly extending members 180a and 180b. Downwardly extending members 178a and 178b are spaced apart in a direction that is perpendicular to the length of cam 64 and handpiece 42, while upwardly extending members 180a and 180b are spaced apart in a direction that is parallel to the length of cam 64 and handpiece 42. Cam follower slots 182a and 182b engage downwardly extending members 178a and 178b of cam transfer 72. Downwardly extending members 178a and 178b of cam transfer 72 may be resilient and may have engagement portions 179a and 179b on their free ends (e.g., hooks or clips) for securely engaging the bottom and side surfaces of cam follower 68.

As best seen in FIG. 20, cannula transfer 74 comprises a sleeve disposed about inner cannula 76. Cannula transfer 74 comprises a proximal end 128, middle section 127, and distal end 126. Upwardly extending members 180a and 180b of cam transfer 72 define fork-shaped structures that receive and cradle middle section 127 of cannula transfer 74. Distal end 126 and proximal end 128 of cannula transfer 74 are disposed outwardly of upwardly extending members 180a and 180b and are shaped to prevent relative translation between cam transfer 72 and cannula transfer 74. In the depicted embodiments, distal end 126 and proximal end 128 of cannula transfer 74 are enlarged relative to middle section 127 to abut the upwardly extending, fork-shaped members 182a and 182b, thereby preventing relative translation between cam transfer 72 and cannula transfer 74. As a result, when cam transfer 72 reciprocates along the length of handpiece 42, cannula transfer 74 reciprocates as well. Because it is affixed to inner cannula 76, when cannula transfer 74 reciprocates, it causes inner cannula 76 to reciprocate within outer cannula 44.

In one exemplary arrangement, motor 62 is a brushed DC motor and may be operably connected to cam 64 in a number of ways. In the embodiment of FIGS. 2 and 3, motor 62 includes a distally extending shaft 66 that extends into a proximal opening 114 and engages recess 116 defined in cam 64. Shaft 66 may be connected to cam 64 via a threaded connection, adhesive, or other known connection means. In an alternate implementation, depicted in FIG. 15, a separate cam coupler 184 is provided. Cam coupler 184 is seated in proximal opening 114 and has a width greater than the diameter of opening 114. Cam coupler 184 is also connected to motor shaft 66 such that rotation of shaft 66 causes cam coupler 184 to rotate, which in turn causes cam 64 to rotate therewith. One revolution of motor shaft 66 causes cam 64 to rotate by one revolution, which in turn causes inner cannula 76 to reciprocate by one complete stroke, i.e., from the position of FIG. 2 to the position of FIG. 3 and back to the position of FIG. 2.

Cam transfer 72 may be connected to cam follower 68 by mechanical means, adhesive means or other known connection means. In one exemplary embodiment, downwardly extending members 178a and 178b mechanically clip onto and removably engage cam follower 68. In another embodiment, cam transfer 72 is adhesively affixed to cam follower 68. In yet another embodiment, both mechanical and adhesive connections are used. The ball bearing (not shown) disposed in cam follower hole 70 traverses cam groove 65 as cam 64 rotates, causing cam follower 68 to reciprocate from the proximal position of FIG. 2 to the distal position of FIG. 3. As a result, cam transfer 72, cannula transfer 74 and inner cannula 76 translate between their respective proximal positions of FIG. 2 and their respective distal positions of FIG. 3 when motor 62 and cam 64 rotate. In certain examples (not separately shown), motor 62 may be connected to a cam follower, and the cam follower may be connected to a cam which is in turn operatively connected to the inner cannula. In accordance with these examples, when the motor rotates, the cam follower rotates and causes the cam to reciprocate, thereby causing the inner cannula to reciprocate.

Figure 14:
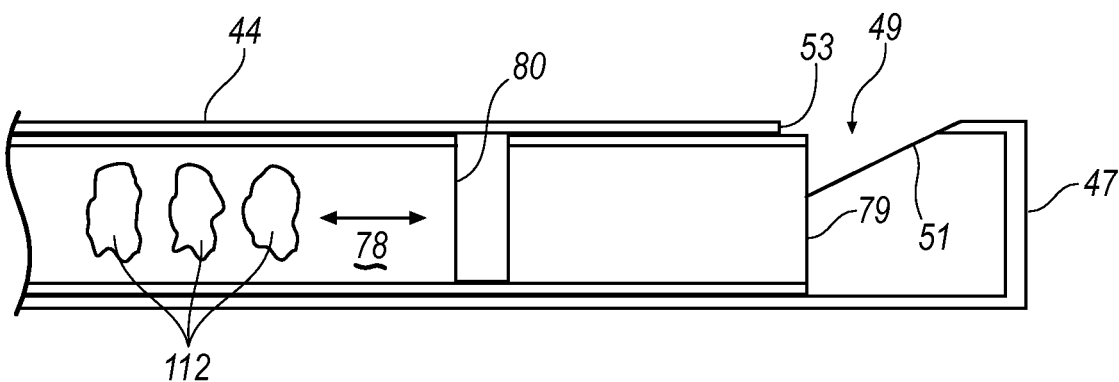
FIG. 14 is a partial cross-sectional view of a distal region of the outer cannula and the inner cannula of the tissue cutting device of FIG. 1, depicting the inner cannula in a second relative position with respect to the outer cannula.

Motor 62 is preferably selected to have a rotational speed that allows inner cannula 76 to reciprocate from the position of FIG. 2 to the position of FIG. 3 and back to the position of FIG. 2 at a rate of at least about 1,000 reciprocations/minute. Reciprocation rates of at least about 1,200 reciprocations/minute are more preferred, and reciprocation rates of at least about 1,500 reciprocations/minute are even more preferred. Reciprocation rates of less than about 2,500 reciprocations/minute are preferred. Reciprocation rates of less than about 2,000 are more preferred, and reciprocation rates of less than about 1,800 reciprocations/minute are even more preferred. As best seen in FIG. 14, the rates of reciprocation of device 40 allow tissue to be severed into "snippets" 112 which are relatively smaller than "slug" tissue samples obtained by many prior devices. As the reciprocation continues, a continuum of severed tissue snippets 112 is obtained.

As mentioned previously, outer cannula 44 includes an opening 49 for receiving tissue into outer cannula lumen 110. As best seen in FIGS. 8-12, opening 49 is preferably defined by a cutting edge 51 that is configured to sever tissue and a non-cutting edge 53 that is not configured to sever tissue. In certain exemplary implementations, non-cutting edge 53 has a radial depth "d" that is no greater than about 50% of the outer diameter of outer cannula 44. In one exemplary implementation, cutting edge 51 is beveled in a radially inward direction, non-cutting edge 53 is not beveled, and cutting edge 51 is located immediately distally of non-cutting edge 53. Inner cannula distal end 79 is preferably configured to cut tissue. In one exemplary embodiment, distal end 79 is beveled in a radially inward direction around the circumference of inner cannula 76 to provide a sharp edge. As tissue is received in outer cannula opening 49, it is compressed between inner cannula distal end 79 and outer cannula cutting edge 51, causing the received tissue to be severed from the surrounding tissue.

Tissue cutting device 40 is particularly well suited for use in cutting tough tissues such as spinal and brain tissues. Outer cannula 44 and inner cannula 76 comprise materials that are generally rigid, such as rigid plastics or metal. In one preferred implementation, both cannulae comprise stainless steel, and more preferably, 304SS typically used in medical grade instruments.

As best seen in FIGS. 9-13, to facilitate the cutting of tough tissues, inner cannula 76 includes a hinge 80. Hinge 80 is located between inner cannula body section 81 which is located on the proximal side of hinge 80 and inner cannula cutting section 83 which is located on the distal side of hinge 80. In one exemplary arrangement, hinge 80 is a living hinge. As used herein, the term "living hinge" refers to a thin, flexible hinge that joins two relatively more rigid parts together. In one example, hinge 80 is a living hinge that is integrally formed with inner cannula body section 81 and inner cannula section 83 by removing a portion of the circumference of the inner cannula 76 along a length L (FIG. 11). Hinge 80 allows cutting section 83 to pivot about hinge 80 as inner cannula 76 reciprocates within outer cannula 44. As inner cannula 76 translates in the distal direction, it contacts tissue received in outer cannula opening 49 and encounters progressively increasing resistance from the tissue as the tissue is urged in the distal direction. As the resisting force of the tissue increases, cutting section 83 pivots progressively more until a zero annular clearance is obtained between inner cannula distal end 79 and outer cannula opening 49. The received tissue is severed and aspirated in the proximal direction along inner cannula lumen 78 and received in tissue collector 58. Thus, inner cannula lumen 78 provides an aspiration path from the inner cannula distal end 79 to the inner cannula proximal end 77. Hinge 80 allows a generally zero annular clearance to be obtained between inner cannula distal end 79 and outer cannula opening 49 at cutting section 83 while not affecting the annular clearance between inner cannula body section 81 and outer cannula 44. This configuration maximizes tissue cutting while minimizing frictional losses that would otherwise occur due to the frictional engagement of the outer surface of inner cannula body section 81 and the inner surface of outer cannula 44 if a very small annular clearance between the outer cannula 44 and inner cannula 76 were present.

Outer cannula opening 49 may have a number of shapes. In certain examples, when outer cannula opening 49 is viewed in plan, it has a shape that is generally square, rectangular, trapezoidal, ovular, or in the shape of the letter "D." In certain other exemplary implementations, outer cannula opening 49 is configured to direct tissue so that it may be compressed as inner cannula 76 translates in the distal direction. In one such implementation, depicted in FIGS. 10 and 12, outer cannula opening 49 has a generally triangular shape when outer cannula opening 49 is viewed in plan. As FIGS. 10 and 12 indicate, when viewed in plan, the width of opening 49 in a direction transverse to the outer cannula longitudinal axis varies longitudinally along the length of outer cannula 44, and preferably narrows from the proximal to distal portions of opening 49. When viewed in side elevation, cutting edge 51 slopes in a radially outward direction moving distally along edge 51. As a result, as a tissue sample is distally urged within outer cannula opening 49 by the action of inner cannula 76, the tissue is increasingly compressed in the direction of the circumference of inner cannula 76 (or in the direction of the "width" of opening 49 when viewed in plan). To ensure complete cutting, inner cannula distal end 79 preferably travels to a position that is distal of outer cannula opening 49 during a tissue cutting operation, i.e., there is an inner cannula overstroke.

Figure 21A:
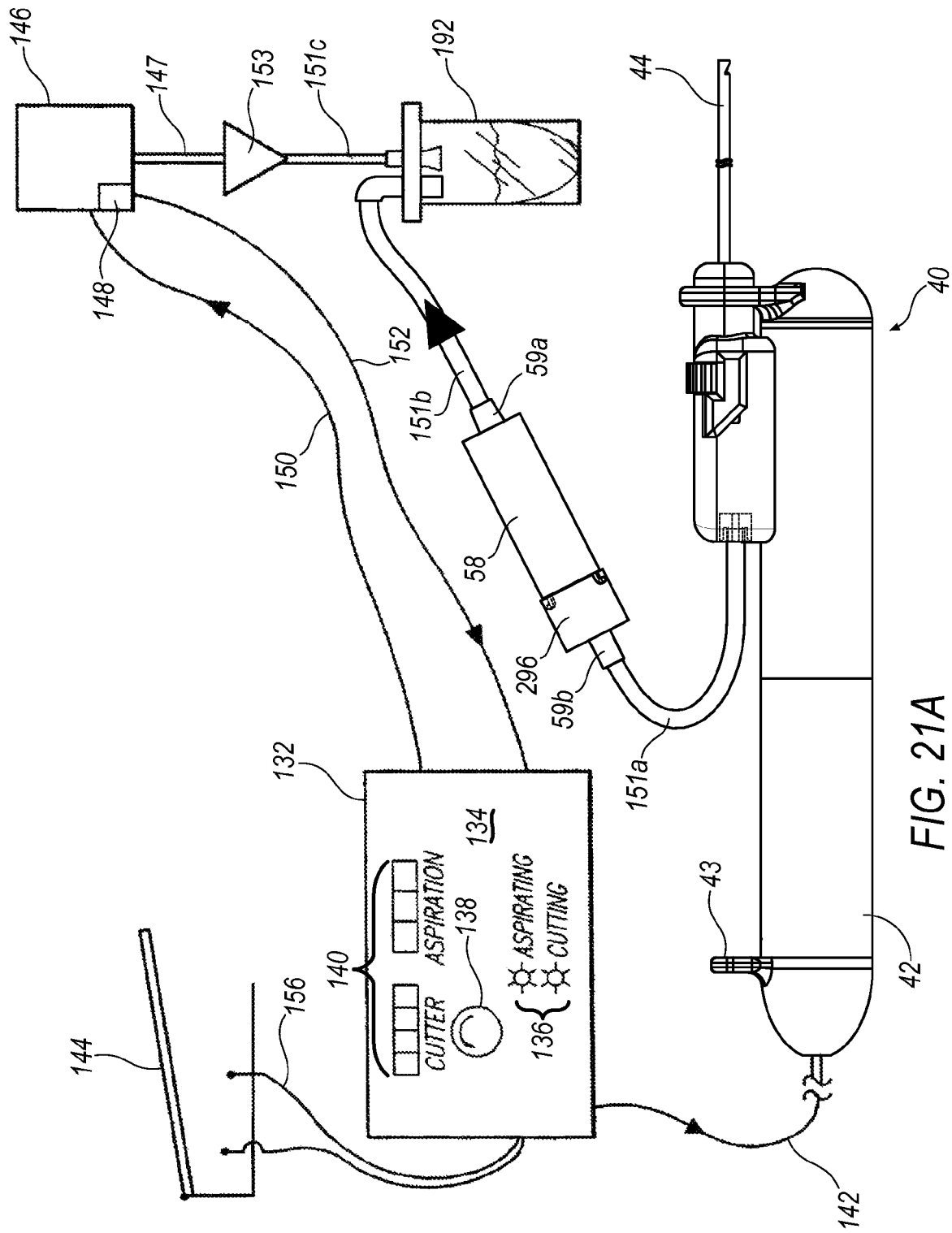
FIG. 21A is a tissue cutting system including a remote tissue collector, control console, foot pedal, and the tissue cutting device of FIG. 1.

As mentioned above, tissue cutting device 40 aspirates tissue samples received in inner cannula lumen 78 to cause the tissue samples to move in the proximal direction along the length of the inner cannula 76. In certain methods of use, device 40 is used to resect tissue without collecting tissue samples for further analysis. In such embodiments, a tissue collector need not be provided. In other embodiments wherein tissue collection is desired, device 40 preferably includes a tissue collector 58 into which aspirated tissue samples are deposited during a tissue cutting procedure. Tissue collector 58 may be located remotely from handpiece 42 and outside the sterile field during a tissue cutting operation as shown in FIG. 21A. However, in an alternative embodiment, as best seen in the examples of FIGS. 1-7, tissue collector 58 is removably connected to handpiece 42. In either embodiment, a fluid collection canister 192 is preferably located between tissue collector 58 and a source of vacuum (such as vacuum generator 153 in FIG. 21A) to protect the vacuum generating apparatus from becoming contaminated or damaged by aspirated fluids. In those embodiments that lack a tissue collector, fluid collection canister 192 may be provided to collect both aspirated fluid and tissue.

Referring to FIGS. 4-7, tissue collector 58 is connected to upper housing 52 proximally of the inner cannula 76 to receive the aspirated tissue samples. Tissue collector 58 is a generally cylindrical, hollow body with an interior volume that is in fluid communication with the inner cannula lumen 78 and a source of vacuum (not shown in FIGS. 4-7). Tissue collector 58 is removably secured to housing connector 96 to allow for the periodic removal of collected tissue samples. Tissue collector 58 is preferably secured to upper housing 52 in a manner that provides a substantially leak-proof vacuum seal to maintain consistent aspiration of severed tissue samples. A vacuum hose fitting 59 is formed on the proximal end of tissue collector 58 and is in fluid communication with the interior of tissue collector 58 and with a vacuum generator, as will be discussed below.

Figure 5:
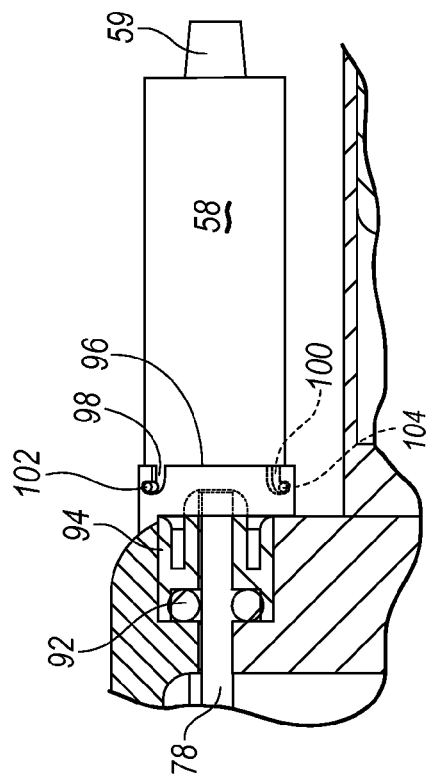
FIG. 5 is a partial cross-sectional view of the tissue cutting device of FIG. 4 in a second configuration in which the device-mounted tissue collector is connected to the tissue cutting device housing.

In the embodiment of FIGS. 4-5, housing connector 96 is a generally cylindrical, flange extending proximally from upper housing 52. Upper shell 54 and lower shell 56 of upper housing 52 cooperatively define a cavity into which a seal holder 94 is partially disposed. Seal holder 94 includes a distal annular recess in which a seal 92, such as an o-ring, is disposed. Seal holder 94 also includes a central lumen through which inner cannula 76 is slidably disposed. A proximally projecting portion 95 of seal holder 94 projects away from upper housing 52 in the proximal direction and is received within housing connector 96. As best seen in FIGS. 2 and 3, inner cannula proximal end 77 preferably remains within seal holder 94 as inner cannula 76 reciprocates during operation of tissue cutting device 40. However, proximal end 77 moves within seal holder 94 as inner cannula 76 reciprocates. Seal 92 preferably comprises a resilient material such as an elastomeric material. The sealing engagement of seal 92 and inner cannula 76 prevents air or fluids from leaking between inner cannula 76 and upper housing 52 and aids in maintaining consistent aspiration of samples through the inner cannula lumen 78.

Housing connector 96 includes connecting features 98 and 100 which are configured to engage with corresponding connecting features 102 and 104 on tissue collector 58. In the embodiment of FIGS. 4 and 5, connecting features 98 and 100 are "J" shaped slots formed in housing connector 96, and connecting features 102 and 104 are complementary protrusions formed on tissue collector 58 which engage connecting features 98 and 100, respectively. To connect tissue collector 58 to housing connector 96, protrusions 102 and 104 are aligned with slots 98 and 100, and tissue collector 58 is then inserted into housing connector 96 in the distal direction. Tissue collector 58 is then rotated to fully engage protrusions 102 and 104 with slots 98 and 100. A seal 103 is provided around the circumference of tissue collector 58 to sealingly engage the inner surface of housing connector 96.

Figure 6:
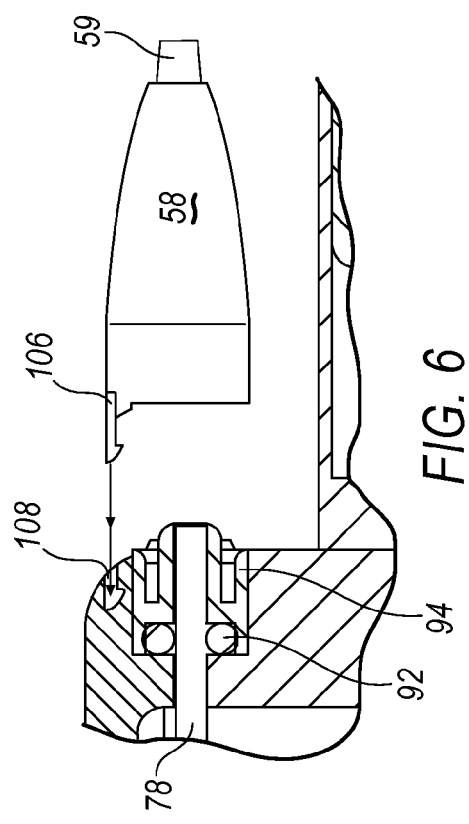
FIG. 6 is a partial cross-sectional view of an alternate embodiment of the tissue cutting device of FIG. 1 in a first configuration in which the device-mounted collector is disconnected from the tissue cutting device.
Figure 7:
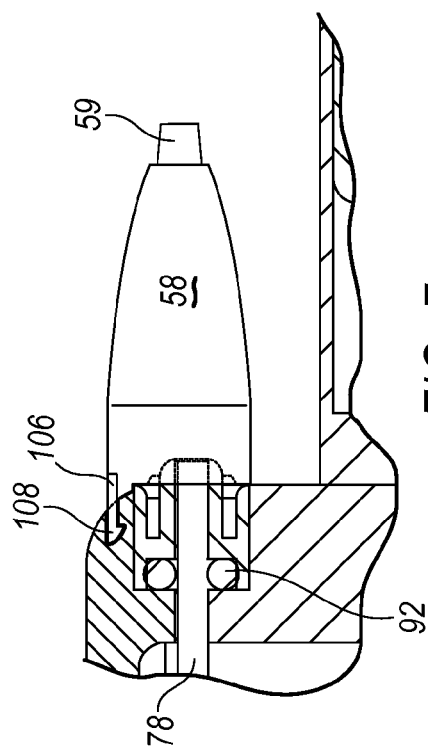
FIG. 7 is a partial cross-sectional view of the tissue cutting device of FIG. 6 in a second configuration in which the device-mounted tissue collector is connected to the tissue cutting device.
Figure 13:
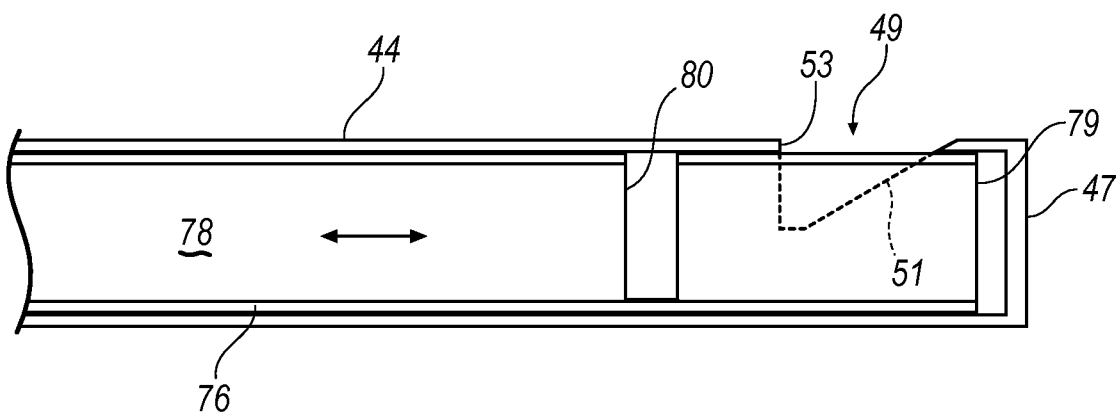
FIG. 13 is a partial cross-sectional view of a distal region of the outer cannula and the inner cannula of the tissue cutting device of FIG. 1, depicting the inner cannula in a first relative position with respect to the outer cannula.

An alternate embodiment of tissue collector 58 is depicted in FIGS. 6 and 7. In the embodiment of FIGS. 6 and 7, tissue collector 58 is semi-elliptical in cross-section and includes a hollow interior for receiving samples, as in the embodiment of FIGS. 4 and 5. In the embodiment of FIGS. 6 and 7, a cylindrical flange housing connector 96 is not provided. Instead, upper housing 52 is formed with an engagement recess 108 that engages a complementary clip 106 formed on tissue collector 58. In each of the foregoing embodiments, tissue collector 58 may be provided with a filter (not shown) in its interior for collecting solid tissue samples while allowing liquids and gases (e.g., air) to pass through. Exemplary filters include medical grade mesh filters with a mesh size smaller than that of tissue snippets 112.

In the embodiments of FIGS. 4-7, tissue collector 58 preferably has a longitudinal axis that is not collinear with the longitudinal axes of handpiece lower housing 50, motor 62, and cam 64. The longitudinal axis of tissue collector 58 is preferably substantially coaxial with the longitudinal axis of inner cannula 76 to yield an "in-line" filter configuration. Tissue collector 58 and inner cannula 76 are both spaced apart from and substantially parallel to the longitudinal axes of handpiece lower housing 50, motor 62, and cam 64. Thus, the cutting axis (i.e., the outer cannula longitudinal axis) and sample aspiration path axis are not coaxial with the longitudinal axis of the handpiece lower housing 50. As a result, when device 40 is used to cut tissue, the surgeon's view of the cutting axis is not obstructed by his or her hand. In addition, the surgeon can treat the proximal end of the filter as a "gun sight" and align it with a tissue sample to be cut to thereby align the outer cannula 44 with the tissue sample, providing enhanced ergonomic benefits over previous devices, in particular, previous neurosurgical devices. In the case of a device with a remote tissue collector 58 such as the one depicted in FIGS. 21A and 21B, the user can treat the proximal end of upper housing 52 as a gun sight and align it with a target tissue.

Figure 18:
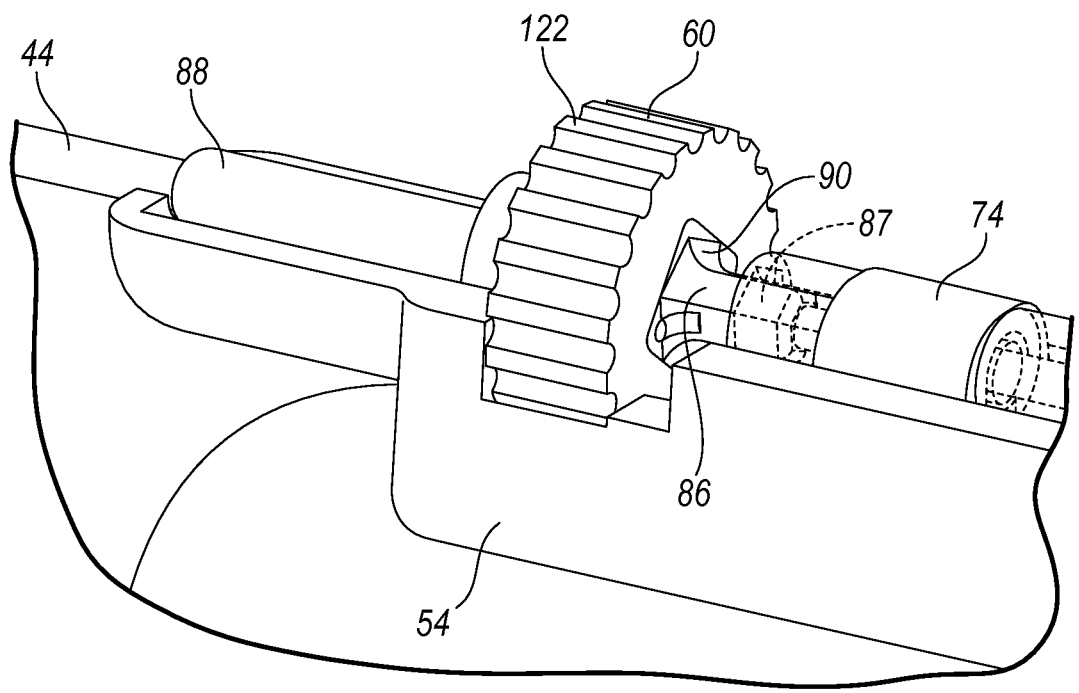
FIG. 18 is a partial perspective view of a portion of the tissue cutting device of FIG. 1 with an upper shell of an outer sleeve upper housing removed to show a dial for rotating the outer cannula.
Figure 19:
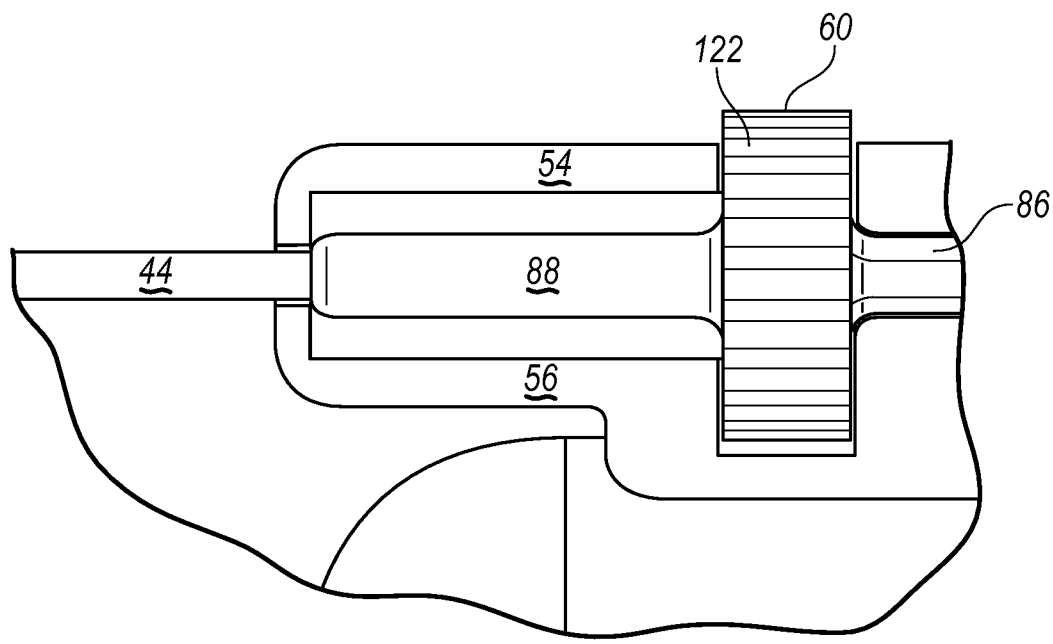
FIG. 19 is a partial side cross-sectional view of the portion of the tissue cutting device of FIG. 18.

When device 40 is used to cut tissue, outer cannula opening 49 must be aligned with the target tissue of interest to receive it for cutting. The entire device 40 can be rotated about the longitudinal axis of handpiece 42 to place outer cannula opening 49 at the desired location. However, this technique can be awkward and may reduce the surgeon's dexterity. Thus, in an exemplary embodiment, device 40 includes a selectively rotatable outer cannula 44. As best seen in FIGS. 18-20, a rotation dial 60 is provided and is rotatably seated in a cavity defined by upper shell 54 and lower shell 56 of upper housing 52. Rotation dial 60 is configured such that when it is rotated, it causes outer cannula 44 to rotate about its longitudinal axis. Rotation dial 60 is preferably connected to an outer cannula connector portion 88. In the embodiment of FIGS. 18-20, outer cannula connector portion 88 is a sleeve that is integrally formed with rotation dial 60 and which is fixedly secured to outer cannula 44 such as by an adhesive or other known connection means. In the exemplary embodiment of FIG. 20 rotation dial 60 has an outer diameter that is greater than that of sleeve 88.

As mentioned previously, inner cannula 76 includes a hinge 80 to allow inner cannula cutting section 83 to pivot toward outer cannula opening 49 when device 40 is in operation. In order to ensure the correct operation of hinge 80, the circumferential alignment of hinge 80 and outer cannula opening 49 should be maintained. Thus, rotation dial 60 is preferably connected to inner cannula 76 such that when rotation dial 60 is rotated, both outer cannula 44 and inner cannula 76 rotate in a fixed angular orientation with respect to one another by an amount that directly corresponds to the amount by which rotation dial 60 is rotated. Rotation dial 60 may be directly connected to inner cannula 76 or may use an intervening connecting device. However, rotation dial 60 should be configured to allow inner cannula 76 to reciprocate with respect to rotation dial 60. As best seen in FIG. 20, rotation dial inner cannula connector 86 may be provided to connect rotation dial 60 to inner cannula 76. Rotation dial inner cannula connector 86 comprises a proximal sleeve 87 disposed about inner cannula 76 and a distal, radially extending annular flange 90 with an outer diameter greater than that of the sleeve 87. Sleeve 87 and flange 90 may be in the shape of circular cylinders. Alternatively, and as shown in FIGS. 18-19, sleeve 87 and flange 90 may be in the shape of a polygonal cylinder. Sleeve 87 is slidably received within the annular cavity 130 at the distal end 126 of the cannula transfer 74 and keyed to the inner surface of cannula transfer 74 at annular cavity 130 such that sleeve 87 can reciprocate with respect to cannula transfer 74 while causing cannula transfer 74 to rotate with sleeve 87 when rotation dial 60 is rotated. When inner cannula 76 is reciprocated, cannula transfer distal end 126 reciprocates with respect to sleeve 87, thereby variably adjusting gap "G" defined within annular cavity 130 (FIG. 20). Alternatively, cannula transfer distal end 126 may be slidably received in an annular cavity formed in sleeve 87 and may be keyed to the inner surface of the annular cavity so that cannula transfer may reciprocate with respect to sleeve 87 while still rotating with sleeve 87 when dial 60 is rotates.

As best seen in FIG. 20, rotation dial 60 includes a first annular cavity 61 that is sized to receive and engage flange 90 in a close fitting relationship. Rotation dial 60 may be press fit to flange 90. In addition, adhesive connections or mechanical connections may be used. Because rotation dial 60 is directly or indirectly connected to both outer cannula 44 and inner cannula 76, both cannulae rotate in direct correspondence to the rotation of rotation dial 60, thereby allowing the user to adjust the orientation of outer cannula opening 49 and inner cannula hinge 80 in a circumferential direction with respect to handpiece 42. As a result, surgeons need not rotate the entire tissue cutting device 40 to obtain the desired angular orientation.

Rotation dial 60, outer cannula 44, and inner cannula 76 are preferably configured for 360° rotation. In addition, tactile indicators are preferably provided on rotation dial 60 to allow a user to reliably determine the extent to which dial 60 has been rotated from a given starting point. The tactile indication may comprise surface features defined on or in the exterior surface of rotation dial 60. In one exemplary embodiment, depicted in FIGS. 18-20, a plurality of ridges 122 is provided around the circumference of rotation dial 60 to provide tactile indication. The ridges also act as grips and facilitate the surgeon's ability to rotate the dial 60 without transferring unwanted motion to the surgical site.

As mentioned previously, vacuum (sub-atmospheric pressure) is applied to tissue collector 58 to aspirate severed tissue samples through inner cannula 76 in the proximal direction. The application of vacuum to inner cannula 76 via tissue collector vacuum hose fitting 59 will have a propensity to produce a vacuum at proximal end 45 of outer cannula 44 if leakage occurs between inner cannula 76 and the components of upper housing 52. The generation of a vacuum at outer cannula proximal end 45 will in turn cause fluids and/or tissue samples at the distal end of outer cannula 44 to flow into the annular clearance between inner cannula 76 and outer cannula 44 that extends from its proximal end at outer cannula proximal end 45 to its distal end at inner cannula distal end 79. This fluid and/or tissue can result in blockage of the annular clearance and increased friction between the inner cannula 76 and outer cannula 44, resulting in degraded performance. Accordingly, a seal 129 is preferably provided to prevent air artifacts, fluid (water, saline, blood, etc.) flow, and tissue sample flow in the annular clearance between inner cannula 76 and outer cannula 44. The seal 129 is preferably disposed adjacent the proximal end of the annular clearance between inner cannula 76 and outer cannula 44, i.e., proximally adjacent to outer cannula proximal end 45. As shown in FIG. 20, seal 129 is preferably annular and circumscribes inner cannula 76, extending from the outer surface of inner cannula 76 in a radially outward direction as well as longitudinally along a portion of the length of inner cannula 76.

In the embodiment of FIG. 20, rotation dial 60 and sleeve 87 act as a seal housing and include a seal cavity 131 which is an annular cavity disposed immediately adjacent to and distal of first annular cavity 61. Seal cavity 131 is sized to accept seal 129 therein. The seal 129 may be a conventional seal such as a solid, flexible and/or elastomeric o-ring. However, seal 129 is preferably amorphous and comprises a thixotropic material that is a semi-solid. It is further preferred that seal 129 fill the entirety of seal cavity 131 to ensure that cavity 131 is substantially leak free. In the exemplary embodiment of FIG. 20, seal cavity 131 has an outer diameter that is greater than the outer diameter of outer cannula 44. Moreover, the annular thickness of seal cavity 131 is preferably greater than the annular clearance between outer cannula 44 and inner cannula 76 to better ensure complete sealing of the annular clearance.

In one exemplary embodiment, seal 129 is a grease—such as the so-called "high vacuum greases"—that is formulated to withstand vacuum conditions. Suitable high vacuum greases include halogenated polymers. The halogenated polymers are preferably based on cyclic ethers or unsaturated hydrocarbon polymeric precursors. In one exemplary embodiment, a perfluoropolyether (PFPE) grease is used. Examples of such greases include the FOMBLIN® family of greases supplied by Solvay Solexis, Inc. Other examples of such greases include polytetrafluroroethylene greases ("PTFE") such as TEFLON® greases supplied by DuPont. One suitable high vacuum grease is FOMBLIN® Y VAC3 grease, which is a PFPE grease with a PTFE thickener. The semi-solid seal 129 preferably has a kinematic viscosity at 20° C. of at least about 500 cSt, more preferably at least about 800 cSt, and even more preferably at least about 1200 cSt. Semi-solid seal 129 preferably has a kinematic viscosity at 20° C. of no greater than about 2500 cSt, more preferably no greater than about 2000 cSt, and even more preferably no greater than about 1700 cSt.

The use of a semi-solid seal 129 has several advantages. Because the seal is semi-solid, it will tend to absorb and dampen vibrations transmitted from the reciprocation of the inner cannula, thereby reducing overall vibration of device 40, and in particular, the vibration transmitted to outer cannula 44. The dampening of such vibrations is particularly beneficial because it prevents unwanted vibration of outer cannula 44 which can disturb delicate neurosurgical procedures. Moreover, because it is not a solid seal, seal 129 will experience less heating and wear as it is frictionally engaged by the reciprocating inner cannula 76. In certain embodiments, a portion of seal 129 will adhere to the outer surface of inner cannula 76 as it reciprocates producing a zero slip velocity condition at the inner cannula 76 outer surface which may further reduce frictional heating and degradation of seal 129. Because semi-solid seal 129 produces less frictional resistance to the reciprocation of inner cannula 76 as compared to conventional solid seals such as o-rings, it also decreases the required motor power consumption and can facilitate the use of lower torque and lower cost motors, which in turn facilitates making device 40 disposable.

Figure 21B:
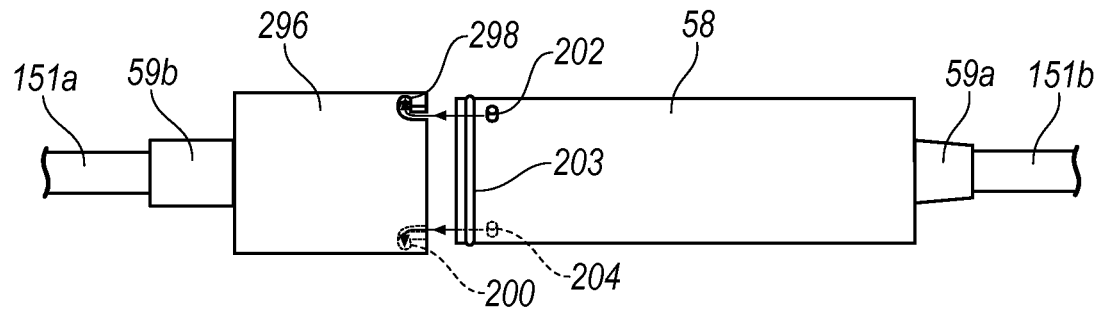
FIG. 21B is an enlarged view of the remote tissue collector of FIG. 21A.

In one configuration, device 40 is connected to a vacuum source and configured for variable aspiration, i.e., configured to supply variable levels of vacuum to inner cannula lumen 78. As depicted in FIG. 21A, in one exemplary implementation, a tissue cutting system is provided which comprises tissue cutting device 40, a tissue collector 58, a controller 132, a vacuum generator 153, a vacuum actuator 144, a controllable valve 146, a vacuum line 151, and a fluid collection canister 192. As mentioned previously, in FIG. 21A tissue collector 58 is located remotely from handpiece 42 and may be placed far enough from the handpiece 42 to remain outside of the sterile field during a tissue cutting operation. As best seen in FIG. 21B, tissue collector 58 is generally the same as the tissue collector 58 depicted in FIGS. 4-5. Vacuum line 151*a* connects the distal end of tissue collector 58 to proximally projecting portion 95 of seal holder 94 on the proximal end of tissue cutting device upper housing 52. In one arrangement, the proximal end of vacuum line 151*a* includes a hose fitting 59*b* that is integrally formed with a tissue collector coupler 296. Coupler 296 is similar in structure to tissue collector connector 96 (FIGS. 4-5) and is a cylindrical structure with a hollow interior for receiving a portion of tissue collector 58. As best seen in FIG. 21B, tissue collector 58 includes projections 202 and 204 which engage complementary slots 298 and 200 in coupler 296 in the same manner that projections 102 and 104 engage slots 98 and 100 in FIGS. 4-5. At the proximal end of tissue collector 58, hose fitting 59*a* engages vacuum line 151*b* which in turn is connected to fluid collection canister 192. Fluid collection canister 192 is connected to vacuum generator 153 via vacuum line 151*c*. Vacuum generator 153 is connected to controllable valve 146 by way of pressure line 147.

The outlet of tissue collection canister 192 is preferably substantially liquid free and is connected to vacuum generator 153 via vacuum line 151*c*. Thus, vacuum generator 153 is in fluid communication with tissue collector 58 and inner cannula lumen 78, thereby generating a vacuum at the proximal end 77 of inner cannula 76 to aspirate severed tissue samples from inner cannula distal end 79 to tissue collector 58. The level of vacuum generated by vacuum generator is preferably variable and selectively controllable by a user. Maximum vacuum levels of at least about 0 in Hg. are preferred, and maximum vacuum levels of at least about 1 in Hg. are more preferred. Maximum vacuum levels of at least about 5 in Hg. are even more preferred, and maximum vacuum levels of at least about 10 in Hg. are still more preferred. Maximum vacuum levels of at least about 20 in. Hg. are yet more preferred, and vacuum levels of at least about 29 in. Hg. are most preferred.

The controllable valve 146 and the vacuum generator 153 provide a means for continuously adjusting and controlling the level of vacuum applied to tissue collector 58 and the proximal end of inner cannula lumen 78. Controllable valve 146 is supplied with a pressurized gas, preferably air, or an inert gas such as nitrogen. In one exemplary embodiment, the pressure applied to controllable valve 146 is about 70 psi.

The system further includes an electrical controller 132 which receives and provides signals to the various components to control or monitor their operations. Controller 132 provides control signals to device 40 via motor drive control line signal path 142 to activate or deactivate motor 62. An aspiration valve control line 150 extends from the controller 132 to the controllable valve 146 which provides pressure to the vacuum generator 153. Signals to the controllable valve 146 through line 150 are used to control the amount of vacuum applied to tissue collector 58.

Controller 132 also receives electrical signals from the various components of the system. For instance, a pressure transducer 148 associated with the aspiration controllable valve 146, sends a signal along line 152 to the controller 132. The signal is representative of the pressure supplied through controllable valve 146 to vacuum generator 153. Thus, the transducer 148 provides immediate feedback to the controller which can in turn provide signals to aspiration controllable valve 146.

The user can adjust the system operating parameters by using panel controls such as a console knob 138 and/or one or more depressible controllers, such as a foot pedal 144. In one embodiment, foot pedal 144 can be used to activate the motor 62 in device 40, causing the inner cannula 76 to reciprocate within the outer cannula 44. In another embodiment, foot pedal 144 can be used to control the vacuum level supplied from vacuum generator 153 to tissue collector 58 and inner cannula lumen 78. In another embodiment, foot pedal 144 can be used both to activate motor 62 and to control the vacuum level supplied from vacuum generator 153 to tissue collector 58. In one arrangement foot pedal 144 is configured to variably increase the level of vacuum applied to tissue collector 58 from a minimum level to a maximum level as foot pedal 144 is depressed from a first position to a second position. In such an arrangement, the first position is one in which foot pedal 144 is not depressed all or is only slightly depressed, and the second position is one in which foot pedal 144 is fully depressed. In another embodiment, knob 138 is used to set a preselected maximum vacuum level applied by vacuum generator 153. Thus, by depressing foot pedal 144 from a first fully open position to a second fully closed position, a plurality (preferably a continuum) of vacuum levels can be supplied to tissue collector 58 with the maximum vacuum level being user adjustable via knob 138.

In one exemplary embodiment, foot pedal 144 includes two switches (not shown) for providing variable vacuum and activating motor 62. In one exemplary embodiment, once foot pedal 144 is partially depressed from an open or undepressed position, motor 62 is activated. In accordance with the embodiment, continued depression of foot pedal 144 activates vacuum generator 153. Foot pedal 144 preferably provides continuous movement between a fully open and a fully depressed position which in turn corresponds to a plurality, and preferably a continuum, of vacuum levels that are supplied to inner cannula lumen 78. Once foot pedal 144 is fully depressed, the vacuum level supplied to inner cannula lumen 78 corresponds to a previously selected maximum vacuum level.

In certain illustrative examples, the user will adjust the level of vacuum to achieve a desired level of "traction" in the tissue surrounding the tissue to be severed. As used here in, the term "traction" refers to the exertion of a pulling force on tissue surrounding the target tissue to be severed. In some instances, traction may be visualizable by the surgeon with the use of a magnification instrument, such as a microscope or an endoscope. The level of vacuum will also determine the amount of unsevered tissue that is drawn into outer cannula opening 49, and therefore, the size of the severed tissue snippets 112 (FIG. 14). Therefore, when fine shaving operations are desired, the vacuum level will be a relatively lower level than if debulking (large scale tissue removal) is performed. Of course, the pre-selected maximum vacuum level will also affect the maximum size of tissue that is drawn into outer cannula opening 49, and therefore, will affect the maximum size of severed tissue samples during any one operation. Also, the vacuum level may be adjusted based on the elasticity, fibrotic content, and hardness/softness of the tissue.

Console 134 may also include indicator lights 136, one of which indicates the activation of cutting and one of which indicates the activation of aspiration. Console 134 may further include an analog display 140 with readouts for "aspiration" and "cutter." The "aspiration" read out indicates the vacuum level supplied to tissue collector 58 from vacuum generator 153. The "cutter" read out indicates the speed of reciprocation of inner cannula 76. In one embodiment, a speed sensor is mounted in device 40 to determine the speed of reciprocation of inner cannula 76 and the sensor is input to controller 132.

As mentioned previously, when device 40 is used to perform a cutting operation, inner cannula 76 reciprocates within outer cannula opening 49 to sever tissue received within outer cannula opening 49. When a cutting operation is complete, it may be preferred to have inner cannula 76 come to rest at a position that is proximal of the non-cutting edge 53 of outer cannula opening 49 to ensure that tissue is not trapped between inner cannula distal end 79 and outer cannula cutting edge 51. However, in certain methods of use, tissue cutting device 40 may be used as an aspiration wand without cutting any tissue. In these embodiments, the stop position of the inner cannula distal end 79 within outer cannula opening 49 determines the open area of the outer cannula 44, and therefore, the aspiration levels that can be applied immediately adjacent outer cannula opening 49. Thus, in some preferred embodiments, the inner cannula stop position is user adjustable. Tissue cutting device 40 may be used to aspirate a variety of fluids associated with a neurosurgical procedure, including without limitation blood, saline, cerebrospinal fluid, and lactate ringer's solution. In certain examples, the inner cannula stop position is adjusted to provide a desired degree of aspiration, outer cannula 44 is positioned proximate a target tissue, and vacuum is applied to manipulate the target tissue and draw it into outer cannula opening 49. Outer cannula 44 is then moved to a desired location or orientation, thereby moving the target tissue to the desired location or orientation. Once the target tissue has been satisfactorily manipulated, a cutting operation is initiated. By using device 40 in this manner, target tissues can be drawn away from areas where tissue cutting operations are undesirable, and the cutting can be performed remotely from those areas.

Figure 24:
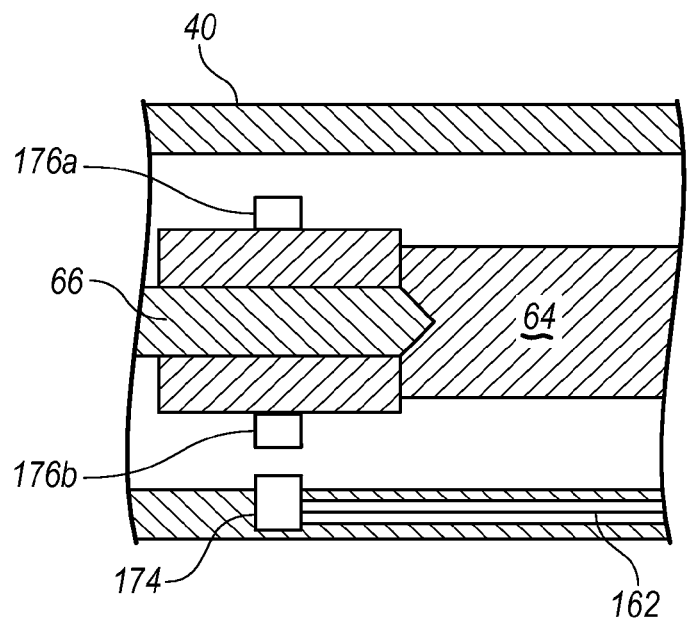
FIG. 24 is a partial cross-sectional view of the tissue cutting device of FIG. 1 depicting motor shaft position sensors for controlling a stop position of an inner cannula.

In one exemplary system, an inner cannula position control is provided which controls the rest position of inner cannula 76 when motor 62 is deactivated. Referring to FIG. 24, cam rotational position indicators 176a and 176b are mounted on the proximal end of cam 64. In an exemplary embodiment, cam rotational position indicators 176a and 176b are magnets having opposite poles. A position sensor 174 is mounted on the inner surface of cam housing 69 and generates a signal indicative of the rotational position of indicators 176a and 176b relative to position sensor 174. As mentioned previously, the rotation of cam 64 correlates directly to the position of inner cannula 76 within outer cannula 44. Thus, the rotation of cam 64 can be sensed to indirectly determine the position of inner cannula 76. Accordingly, indicators 176a/176b and sensor 174 can be used to determine the position of inner cannula 76 with respect to non-cutting edge 53 of outer cannula opening 49 (FIGS. 10-12).

Figure 22:
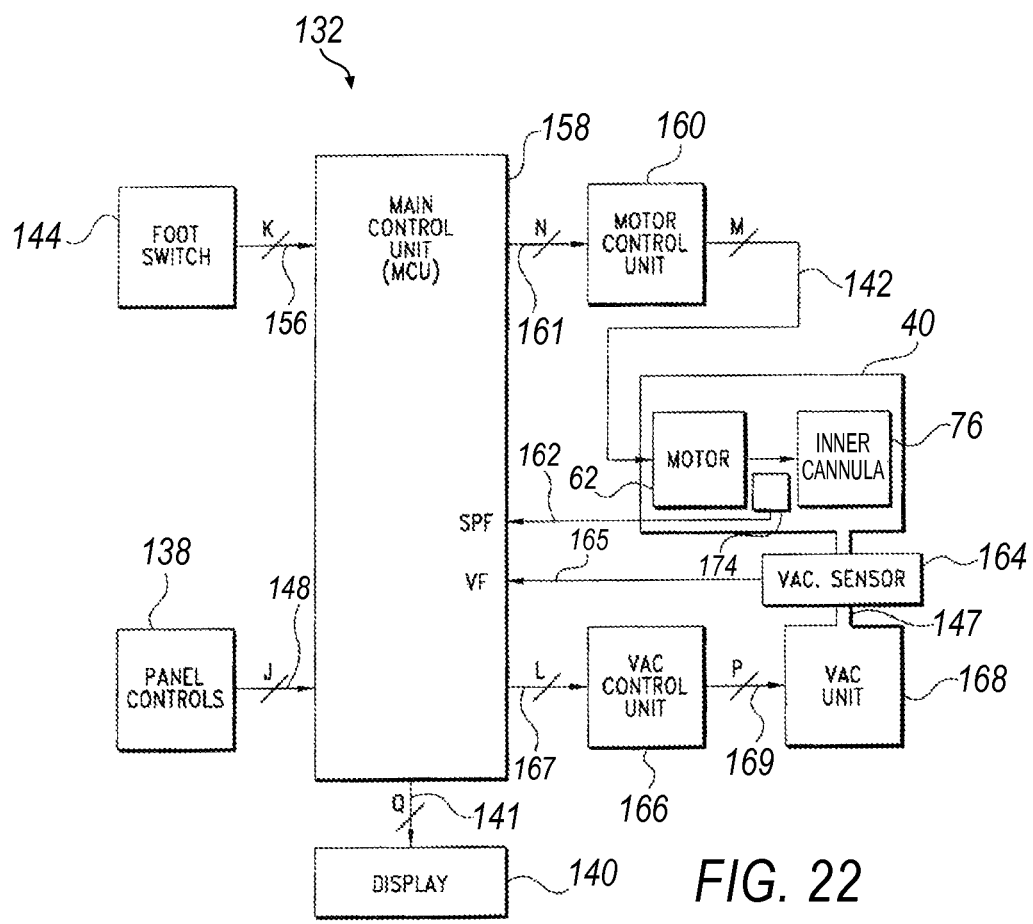
FIG. 22 is a block diagram of a control scheme for the tissue cutting system of FIG. 22.

Referring to FIG. 22, an embodiment of a system for controlling the operation of tissue cutting device 40 is provided. The system includes a main control unit 158 ("MCU"), which (in the embodiment shown) is configured as a microprocessor-based system. In one implementation, MCU 158 is incorporated in controller 132 (FIG. 21A) and is operable to control the various operations of the tissue cutting device 40. Foot switch 144 is electrically connected to a number of inputs of MCU 158 via an equal number, K, of signal paths 156, wherein K may be any integer. Panel controls, such as knob 138, are electrically connected to a number of inputs of MCU 158 via an equal number, J, of signal paths 145, wherein J may be any integer.

Display unit 140 is electrically connected to a number of outputs of MCU 158 via an equal number, Q, of signal paths 141, wherein Q may be any integer. In one exemplary implementation, depicted in FIG. 21A, display unit 140 is provided on console 134.

As mentioned previously, tissue cutting device 40 includes motor 62 coupled to the inner cannula 76 by an inner cannula drive assembly 63. The motor 62 is electrically connected to motor control unit 160 via a number, M, of signal paths 142 wherein M may be any integer. The motor control unit 160 is, in turn, connected to a number of outputs of MCU 158 via an equal number, N, of signal paths 161. Cam rotational position sensor 174 is electrically connected to a motor shaft position feedback input (SPF) of MCU 158 via signal path 162, and provides a motor stop identification signal thereon as will be more fully described hereinafter. The motor shaft stop identification signal provided by sensor 174 on signal path 162 preferably provides MCU 158 with a motor stop identification signal and may optionally provide a cutter speed signal that is proportional to the motor speed for a geared system or identical to the motor speed for a direct drive system.

Tissue cutting device 40 is further mechanically connected to a vacuum unit 168 (e.g., a combination of controllable valve 146 and vacuum generator 153 in FIG. 21A) via conduit 163, whereby the vacuum unit 168 provides a controllable vacuum level to tissue cutting device 40 for aspirating tissue received in inner cannula lumen 78. Vacuum unit 168 is electrically connected to a vacuum control unit 166 via a number, P, of signal paths 169 wherein P may be any integer. The vacuum control unit 166 is, in turn, connected to a number of outputs of MCU 158 via an equal number, L, of signal paths 167, wherein L may be any integer. A vacuum sensor 164, which may be a temperature compensated solid-state pressure sensor, may be positioned within the vacuum line 151 and electrically connected to a vacuum feedback (VF) input of MCU 158 via signal path 165. Alternatively, the vacuum sensor 164 may be disposed within hand piece 42 or within the vacuum unit 168 itself.

In operation, the MCU 158 is responsive to a vacuum command signal, preferably provided by a corresponding control mechanism associated with console 134, foot pedal 144, or an equivalent control mechanism, to provide one or more corresponding vacuum control signals to vacuum control unit 166 along signal paths 167. The vacuum control unit 166, in turn, is responsive to the one or more vacuum control signals to activate the vacuum unit 168 to thereby provide tissue cutting device 40 with a desired level of vacuum. The actual vacuum level provided to tissue cutting device 40 is sensed by vacuum sensor 164, which provides a corresponding vacuum feedback signal to the vacuum feedback input VF of MCU 158. The MCU 158 is then operable to compare the vacuum feedback signal with the vacuum command signal and correspondingly adjust the one or more vacuum control signals to achieve the desired vacuum level within tissue cutting device 40. Such closed-loop feedback techniques are well known in the control systems art.

In one alternative embodiment, the MCU 158 can be replaced by individual microprocessors controlling the input and output for controlling the operation of the motor 62 and the vacuum unit 168. In this alternative embodiment, the motor control and vacuum control microprocessors can be PIC16CXX Series microcontrollers provided by Microchip, Inc. of Chandler Ariz. The motor control microcontrollers can receive input signals from the motor driver circuit 172 (FIG. 23) and position sensor 174, as well as the foot switch 144 and panel controls 132. Likewise, the vacuum microcontroller can receive input signals from the vacuum sensor 164, the foot switch 144 and panel controls 138. Each microcontroller can provide its own output to its driven component and have its own display, such as an LED display, indicative of its operational status. Moreover, the two units can communicate with each other to ensure clean cutting by proper timing of the cutting and aspiration functions.

Figure 23:
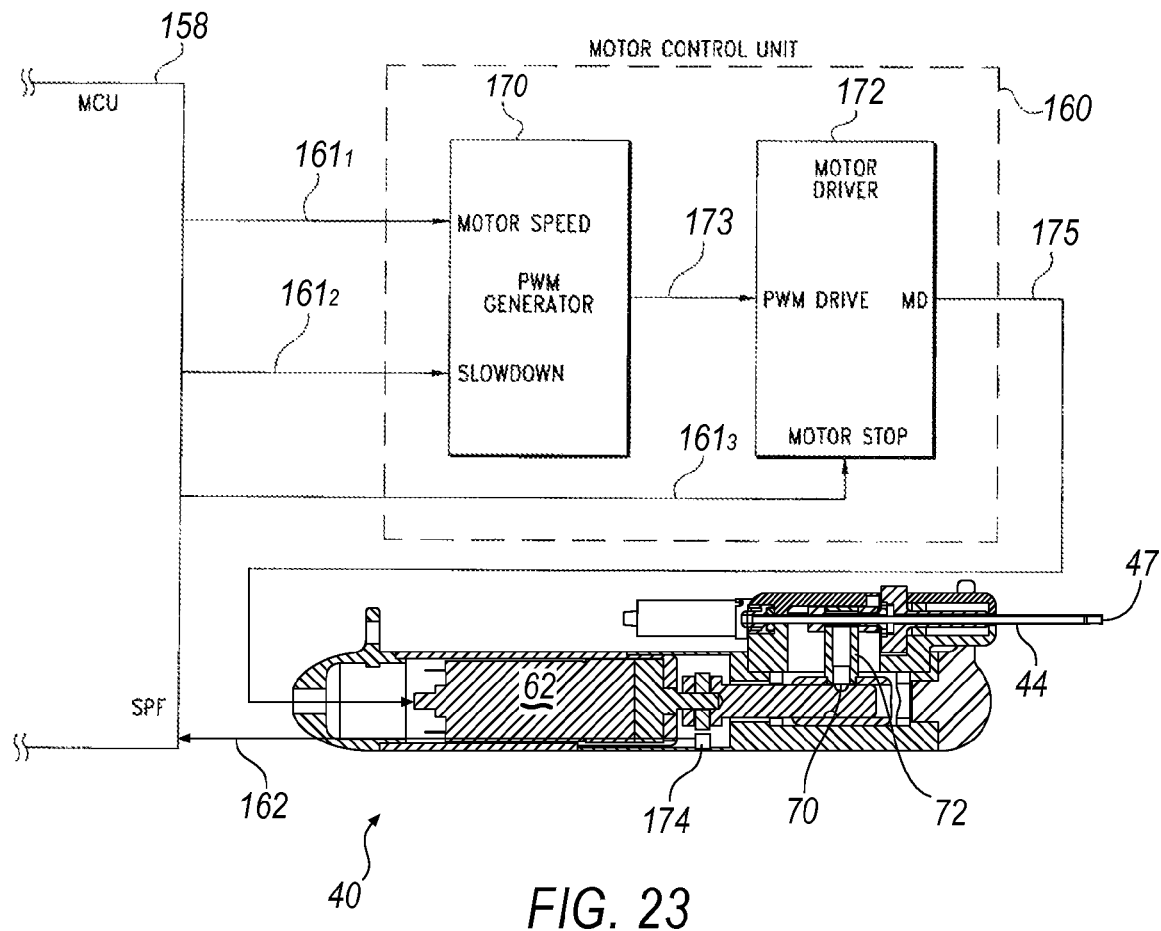
FIG. 23 is diagram of the tissue cutting device of FIG. 1 and the motor control unit of FIG. 22.

Referring now to FIG. 23, one exemplary embodiment of the motor control unit 160 is shown in greater detail. The motor control unit 160 in one embodiment includes a pulse width modulation (PWM) generator circuit 170 having a motor speed input connected to one of the MCU outputs 1611. If motor speed control is provided, the output 1611 can provide a variable voltage signal indicative of a desired motor speed and based upon the position of a throttle, foot pedal, or other actuator. In certain embodiments, an additional input is connected to another one of the MCU outputs 1612. The signal at this output 1612 can be a motor slowdown signal as described below. Alternatively, the output 1612 can constitute a braking signal used in connection with a current feedback motor controller. As a further alternative, the slowdown command may be communicated via the motor speed command itself, rather than through a separate signal 1612. In this instance, the output 1612 may not be required.

In the illustrated embodiment, the PWM is disposed within the motor control unit 160. Alternatively, the PWM can be integrated into the MCU 158, or into the separate motor control microprocessor discussed above. In embodiments that include motor speed control, the motor speed input receives a motor speed signal from MCU 158 indicative of desired operational speed of the motor 62. The slowdown input can receive a speed adjustment signal from the MCU 158 based on an actual motor speed signal provided by a motor sensor associated with the motor 62.

A motor driver circuit 172 is electrically connected to PWM generator circuit 170 via signal path 173 and receives a PWM drive signal therefrom, which is a pulse width modulated signal indicative of desired motor speed. The motor driver circuit 172 provides a motor drive signal (MD) to motor 62 via signal path 175. While the disclosed embodiment contemplates digital control of the motor using the PWM generator circuit 170, alternative embodiments can utilize closed loop feedback analog circuits, particularly where slower cutting speeds are contemplated.

The motor drive signal includes a motor stop input that is connected to another one of the MCU outputs 1611. In accordance with one aspect of the present disclosure, MCU 158 provides a motor stop signal on signal path 1613, based on a motor deactivation command provided by foot switch 144 or panel control 138 and also based on a motor stop identification signal provided by sensor 174, to stop the inner cannula 76 in a desired position, as will be more fully described hereinafter. In certain embodiments, only the motor stop signal is utilized to command the motor to stop at the predetermined position. In these certain embodiments, the motor slowdown signal on path 1612 can be eliminated, or the input on path 1612 can be used for other control signals to the motor control circuit.

Figure 25:
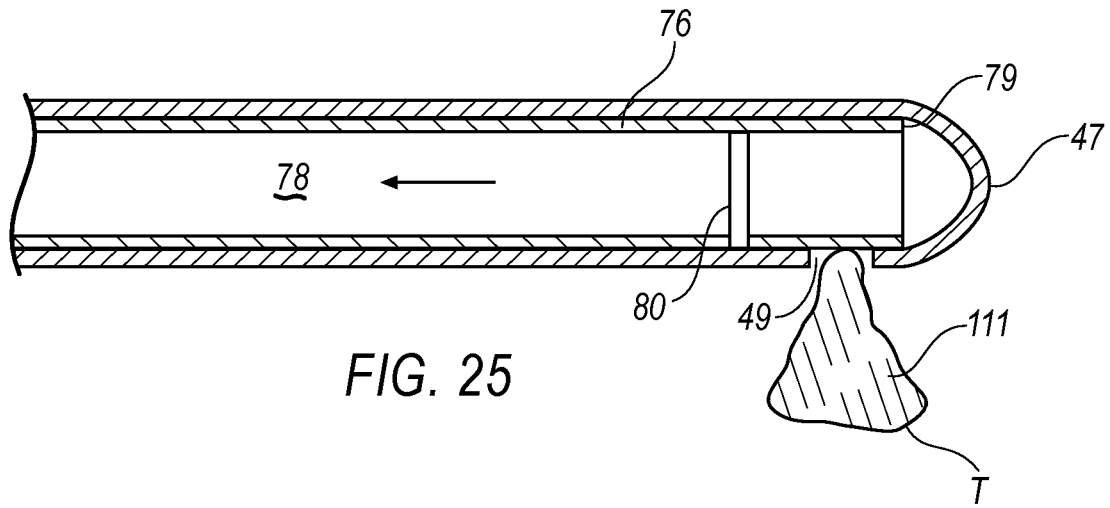
FIG. 25 is a partial cross-sectional view of the outer cannula and inner cannula of the tissue cutting device of FIG. 1 with the inner cannula in a first position relative to the outer cannula.
Figure 26:
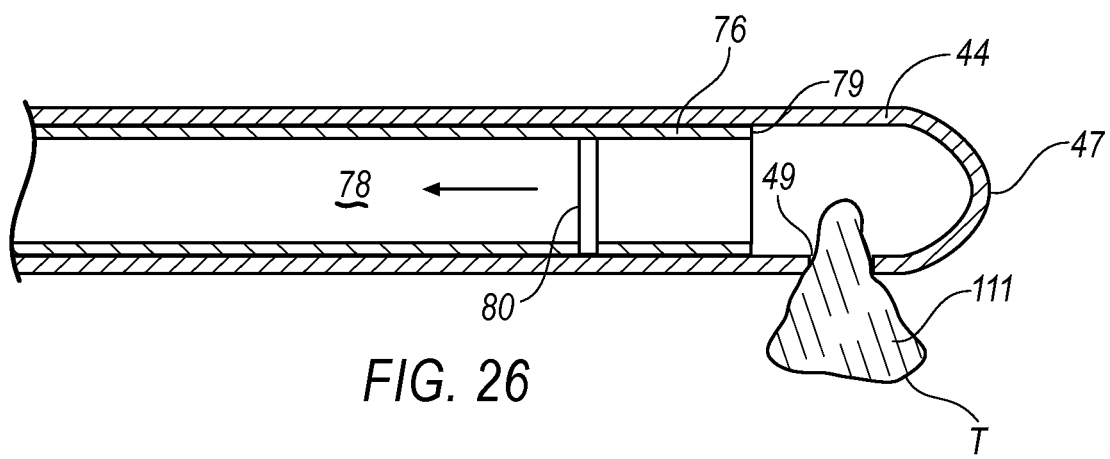
FIG. 26 is a partial cross-sectional view of the outer cannula and inner cannula of the tissue cutting device of FIG. 1 with the inner cannula in a second position relative to the outer cannula.
Figure 27:
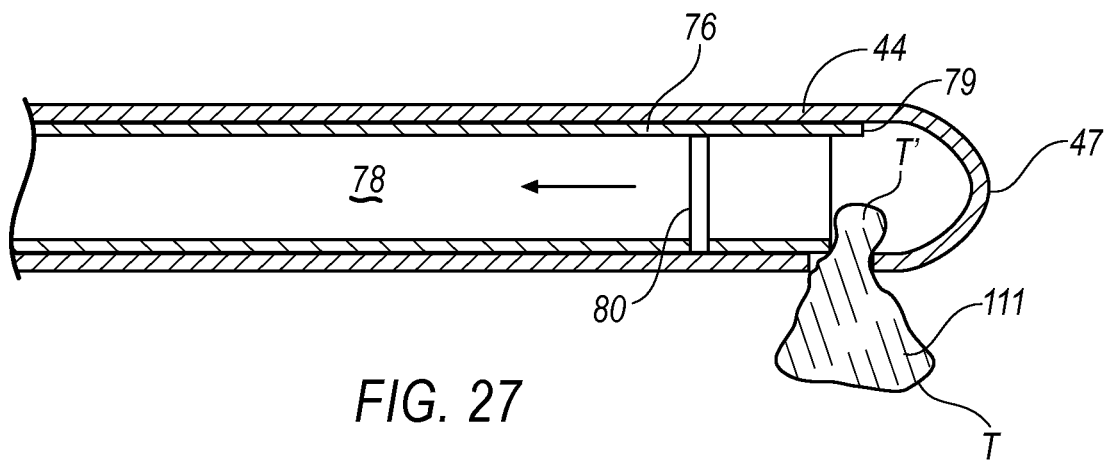
FIG. 27 is a partial cross-sectional view of the outer cannula and the inner cannula of the tissue cutting device of FIG. 1 with the inner cannula in a third position relative to the outer cannula.

As mentioned previously, when tissue cutting device 40 is deactivated, inner cannula 76 may come to rest partially disposed within outer cannula opening 49. Referring to FIGS. 25-27, three different stop positions of inner cannula 76 are shown. FIG. 27 shows that inner cannula 76 can be stopped in a position in which a portion of the tissue T is trapped between the outer cannula opening 49 and the inner cannula distal end 79. Efforts at withdrawing outer cannula 44 from the surgical site may accordingly result in tearing of the tissue portion T' away from the surrounding tissue base T. Surgeons encountering such trapping would typically be required to re-activate tissue cutting device 40 to release the tissue portion T' from the surrounding tissue base T. To prevent such tissue trapping from occurring, deactivation of the motor 62 is controlled in such a manner that the inner cannula distal end 79 is positioned remotely from the outer cannula opening 49 when inner cannula 76 stops reciprocating. However, in certain methods of use, device 40 is used as an aspiration wand. In those methods, the stop position of inner cannula distal end 79 may be adjusted to different locations within outer cannula opening 49 in order to adjust the level of aspiration supplied to a region of the anatomy proximate outer cannula opening 49. For example, stop positions may be selected that limit the percent open area of outer cannula opening 49 to 25%, 50%, or 75% of the total area of opening 49.

Referring again to FIGS. 23 and 24, controlled deactivation of the motor 62 will now be described in detail. When it is desired to deactivate tissue cutting device 40, a motor stop command is provided such as via foot switch 144 or a panel control 138. In one embodiment, MCU 158 is responsive to the motor stop command to provide a slowdown signal to the PWM generator via signal path 1612 which slows the action of motor 62. Preferably, the slowdown signal corresponds to a predefined signal level operable to drive the motor 62 at a motor speed below a motor speed threshold level. Since motor 62 is a brushed DC motor, it has a rotational resistance or resistive torque associated therewith as described above. In addition, in some cases friction between the inner cannula 76 and outer cannula 44 will increase the rotational resistance. Due to this combined rotational resistance, operation of the motor 62 will cease very rapidly or nearly instantly if the motor drive signal on signal path 142 is disabled while driving motor 62 below the motor speed threshold. Accordingly, when device 40 is used to cut tissue, alignment of position indicators 176a or 176b with sensor 174 preferably corresponds to a position of the inner cannula 76 at which there is no danger of trapping tissue between inner cannula distal end 79 and the outer cannula opening 49, and sensor 174 is operable to produce the motor stop identification signal when so aligned with indicator 176a or 176b.

In one embodiment, MCU 158 is operable to produce a motor stop signal on signal path 1613 when sensor 174 detects alignment of position indicators 176a or 176b therewith after one passage thereby of indicator 176a or 176b since producing the slowdown signal on signal path 1612. Allowing one passage of indicator 176a or 176b by sensor 174 after issuing the slowdown signal ensures that the rotational speed of motor 62 is at or below the motor speed threshold when subsequently issuing the motor stop command, regardless of the position of indicator 176a or 176b relative to sensor 174 when the slowdown command was issued. After one passage of indicator 176a or 176b by sensor 174 since issuing the slowdown signal, MCU 158 is responsive to the signal provided by sensor 174 indicative of alignment of indicator 176a or 176b therewith, to produce the motor stop signal on signal path 1613. The motor driver 172 is responsive to the motor stop signal to produce a motor disable signal on signal path 175. Due to the inherent rotational resistance, motor 62 is responsive to the motor disable signal to immediately cease operation thereof with indicator 176a or 176b substantially aligned with sensor 174, and with the inner cannula 76 accordingly positioned so as not to trap tissue between inner cannula distal end 79 and the outer cannula opening 49.

As mentioned above, in one exemplary embodiment, the inner cannula stop position is user adjustable, such as by adjusting a panel control 138 on console 134. In accordance with the embodiment, it is contemplated that the stopped rotational position of cam 64, and therefore the inner cannula distal end 79, may be instead aligned with a predetermined differential distance between the indicator 176a/176b and the sensor 174. The braking characteristics of the inner cannula 76 and motor 62 can be ascertained and the stopping distance determined so that this predetermined differential distance can be calibrated accordingly. However, in a preferred embodiment, when inner cannula 76 comes to rest, the distal end 79 is located proximally of the outer cannula opening 49 by a predetermined distance, as shown in FIG. 26.

A method of using device 40 to perform a tissue cutting procedure will now be described in the context of a neurosurgical procedure involving the cutting of a neurological target tissue. In one example, the target tissue is brain tissue, and in another example the target tissue is spinal tissue, for example, the tissue of an intervertebral disk. In certain exemplary methods, the tissue specimen being cut is a tumor or a lesion.

In accordance with the method, it is first determined whether the cutting operation will be a debulking operation or a fine shaving operation or a cutting operation that is somewhere in between a debulking and fine shaving operation. A surgical access path is then created to the tissue sample of interest. In one embodiment, the surgical path is created and/or the target tissue is accessed using an "open" procedure in which the target tissue is open to the atmosphere (e.g., a full open craniotomy). In another embodiment, the surgical path is created and/or the target tissue is accessed using a "closed" procedure in which the target tissue is sealed from the atmosphere.

At this point, the distal end 79 of inner cannula 76 is located proximally of outer cannula opening 69 due to the use of an inner cannula stop position control of the type described previously. The maximum vacuum level to be applied to device 40 is then set using panel controls 138. Generally, higher vacuum levels will be used for debulking procedures than for fine shaving procedures as higher vacuum levels will tend to draw relatively larger sections of tissue into outer cannula opening 49. In one embodiment, the panel control 138 is a knob on console 134 that is rotated to set the desired maximum vacuum level.

In one arrangement, device 40 is configured to be gripped with a single hand during a tissue cutting procedure. Thus, the surgeon will grasp handpiece 42 in the fingers of one hand and insert outer cannula 44 to a location proximate the target tissue. Depending on the hand and the surgeon's orientation with respect to the target tissue, the surgeon may then rotate dial 60 to rotate outer cannula 44 about its own longitudinal axis and orient outer cannula opening 49 immediately adjacent the target tissue. The rotation of outer cannula 44 with dial 60 causes inner cannula 76 to rotate such that a fixed rotational or angular relationship is maintained between inner cannula 76 and outer cannula 44. Once the opening 49 is in the desired orientation, the motor 62 is activated, for example, by beginning to depress pedal 144 from its fully undepressed (open) position to a second partially depressed position which causes motor control unit 160 to send a signal to motor 62 on signal path 142. Motor 62 may also be activated by a panel control 138. The rotation of motor 62 causes cam 64 to rotate, resulting in the reciprocation of cam follower 68 and cam transfer 72. The reciprocation of cam transfer 72 causes cannula transfer 74 to reciprocate, thereby reciprocating inner cannula 76 within outer cannula lumen 110.

Once motor 62 is activated, vacuum is supplied to inner cannula lumen 78. In one embodiment, as the pedal 144 is further depressed (beyond the position at which motor 62 is activated), vacuum generator 153 is activated. The surgeon then adjusts the degree of depression of the foot pedal 144 to obtain the desired level of vacuum by visualizing the movement of the target tissue relative to the outer cannula opening 49. In certain embodiments, the surgeon controls the vacuum level to obtain a desired amount of traction in the tissue surrounding the target tissue. If the surgeon desires to apply the previously set maximum vacuum level, he or she depresses pedal 144 to its fully depressed position.

If desired, the surgeon may depress and partially release the pedal 144 a number of times to manipulate the target tissue in a satisfactory manner. Open or closed loop vacuum control may be provided. In one example, closed loop control is used. In accordance with the example, vacuum controller 166 is manipulable to adjust the setpoint of vacuum generator 153 which is manipulable to adjust the inner cannula vacuum level along a continuum of levels below the pre-selected maximum level. In one embodiment, the extent of depression of foot pedal 144 dictates the vacuum set point supplied to vacuum control unit 166 on signal path 167, and therefore, the amount of vacuum provided by vacuum unit 168. Vacuum sensor 164 measures the vacuum supplied to tissue collector 58 and feeds a signal back to main control unit 158 on signal path 165. The measured vacuum is then compared to the set point applied to vacuum control unit 166 via foot pedal 144, and the signal transmitted to vacuum generator 153 is then adjusted to move the measured vacuum value towards the set point. To obtain a vacuum level equal to the maximum pre-set level, pedal 144 is completely depressed.

In another example, the vacuum system is operated in an open loop manner. In accordance with the example, pedal 144 directly adjusts vacuum unit 166. In one implementation, pedal 144 variably adjusts the amount of pressure supplied to controllable valve 146. The variation in pressure in turn affects the vacuum provided by vacuum generator 153 to inner cannula lumen 78. As with the closed loop example, the system may be configured to allow the user to set a maximum vacuum that is obtained when pedal 144 is fully depressed.

Maximum vacuum levels of at least about 0 in Hg. are preferred, and maximum vacuum levels of at least about 1 in Hg. are more preferred. Maximum vacuum levels of at least about 5 in Hg. are even more preferred, and maximum vacuum levels of at least about 10 in Hg. are still more preferred. Maximum vacuum levels of at least about 20 in. Hg. are yet more preferred, and vacuum levels of at least about 29 in. Hg. are most preferred.

Due to the resistance of the tissue drawn into outer cannula opening 49, cutting section 83 pivots about hinge 80 and toward outer cannula opening 49 as inner cannula 76 travels in the distal direction. The inner cannula cutting section 83 continues to pivot as it travels in the distal direction, eventually compressing tissue within outer cannula opening 49 and severing it. The severed tissue forms a continuum of tissue snippets 112 (FIG. 14) within inner cannula lumen 78.

Due to the vacuum applied to tissue collector 58, snippets 112 are aspirated through inner cannula lumen 78 in the proximal direction. They eventually exit inner cannula lumen 78 at inner cannula proximal end 77 and enter tissue collector 58 (or fluid collection canister 192 if no collector 58 is provided). Any fluids that are aspirated exit tissue collector 58 and are trapped in fluid collection canister 192. The surgeon preferably severs tissue at a cutting rate of at least about 1,000 cuts/minute. Cutting rates of at least about 1,200 cuts/minute are more preferred, and cutting rates of at least about 1,500 cuts/minute are even more preferred. Cutting rates of less than about 2,500 cuts/minute are preferred. Cutting rates of less than about 2,000 are more preferred, and cutting rates of less than about 1,800 cuts/minute are even more preferred.

The surgeon may move device 40 around the target tissue until the desired degree of cutting has been completed. Motor 62 is then deactivated, for example, by completely releasing pedal 144 so it returns to its fully undepressed (open) position. If an inner cannula stop position control is provided, inner cannula 76 preferably comes to rest proximally of outer cannula opening 49, as shown in FIG. 26. Outer cannula 44 is then removed from the surgical site. Tissue collector 58 is then removed from upper housing 52 of handpiece 42, and the collected tissue samples are either discarded or saved for subsequent analysis. Fluids collected in canister 192 are preferably discarded. If the remote tissue collector of FIG. 21A is used, tissue samples may be removed from it without removing outer cannula 44 from the surgical site or otherwise disturbing the surrounding tissue.

Figure 28:
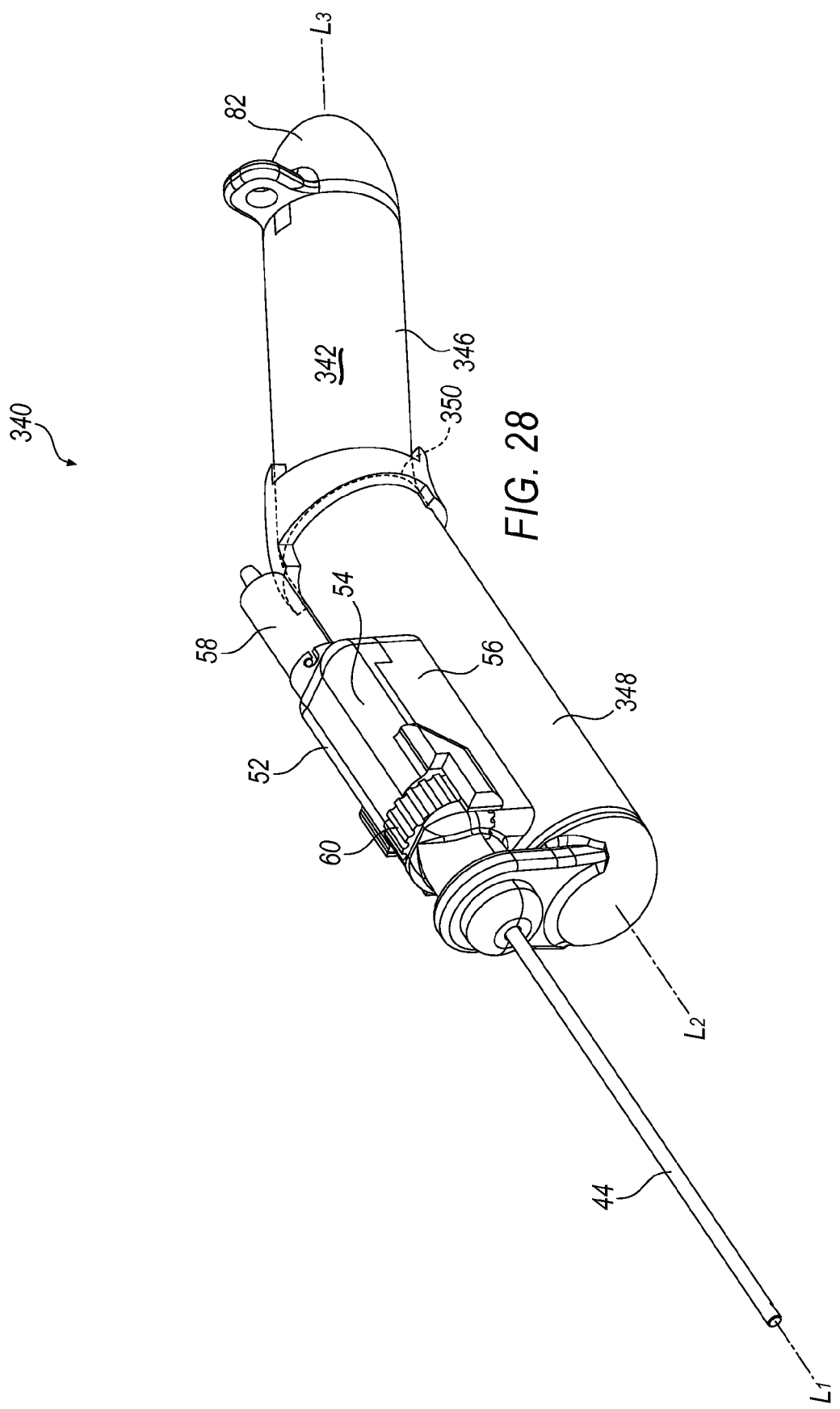
FIG. 28 is a perspective view of a tissue cutting device with an angled handpiece in accordance with a second embodiment.
Figure 29:
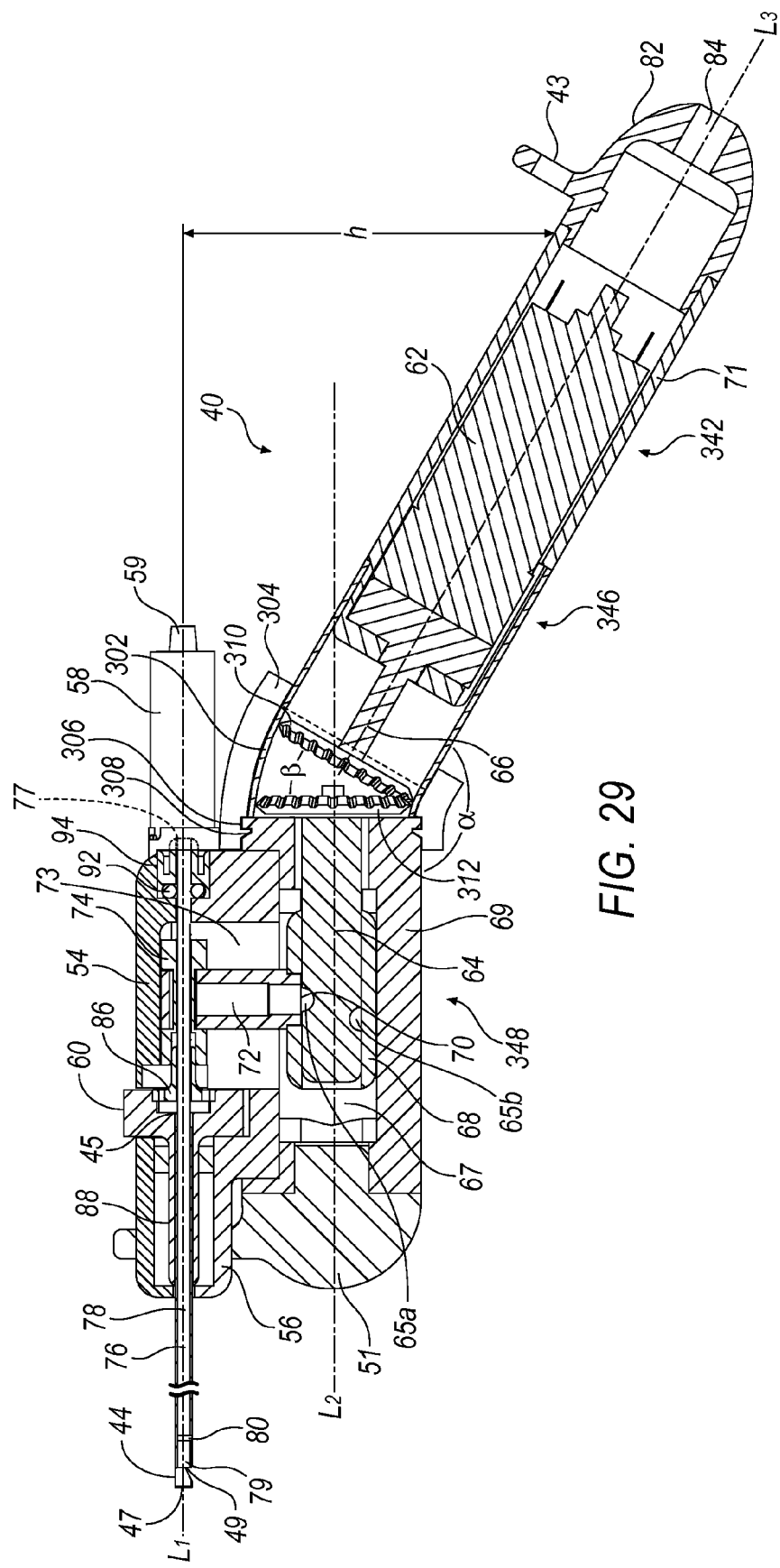
FIG. 29 is a cross-sectional view of the tissue cutting device of FIG. 28 depicting an inner cannula in a first relative position with respect to an outer cannula in which the inner cannula's distal end is located proximally of the outer cannula's distal end.
Figure 30:
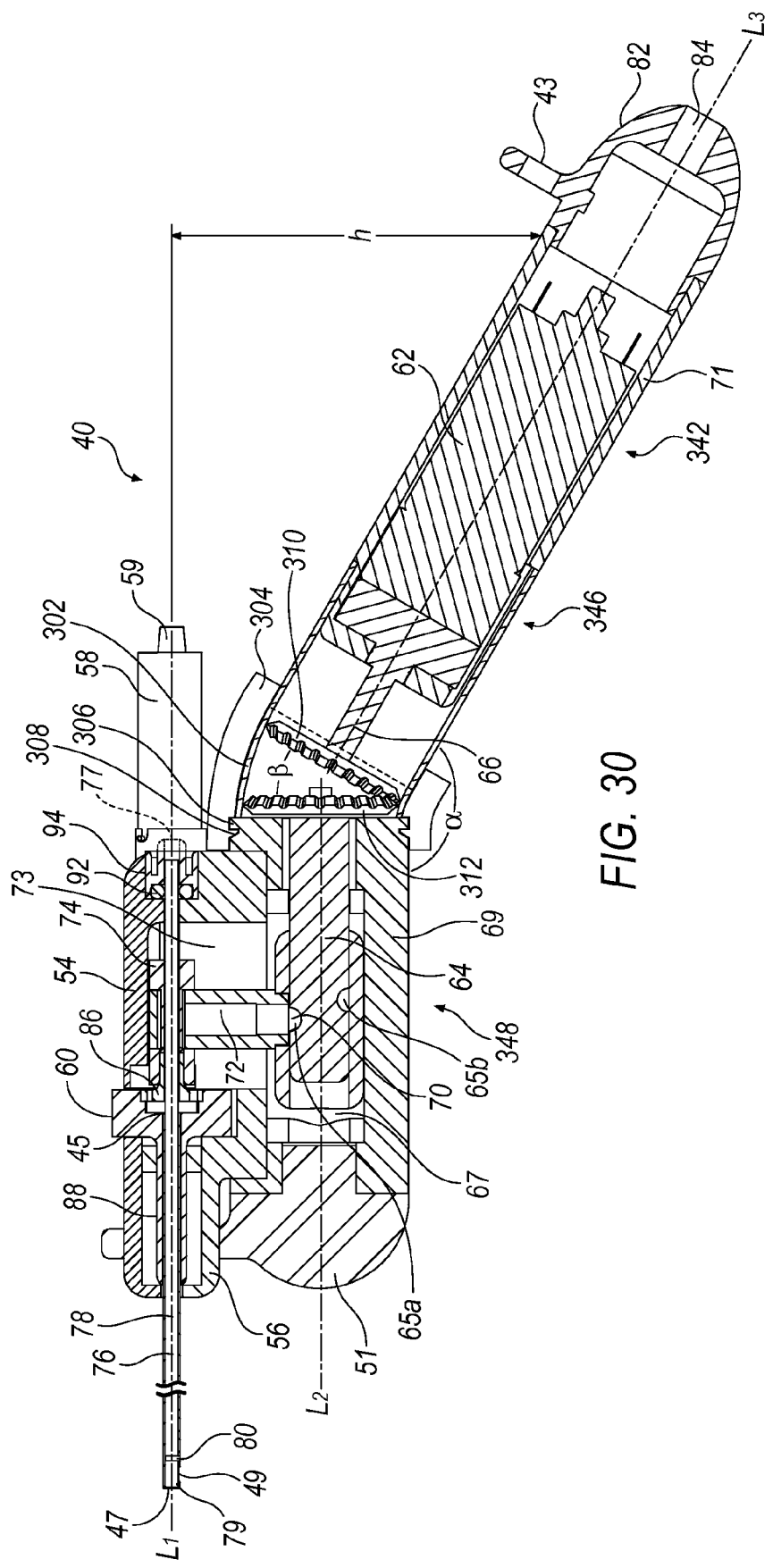
FIG. 30 is a cross-sectional view of the tissue cutting device of FIG. 28 depicting the inner cannula in a second relative position with respect to the outer cannula in which the inner cannula's distal end is located at the distal end of the outer cannula.
Figure 31:
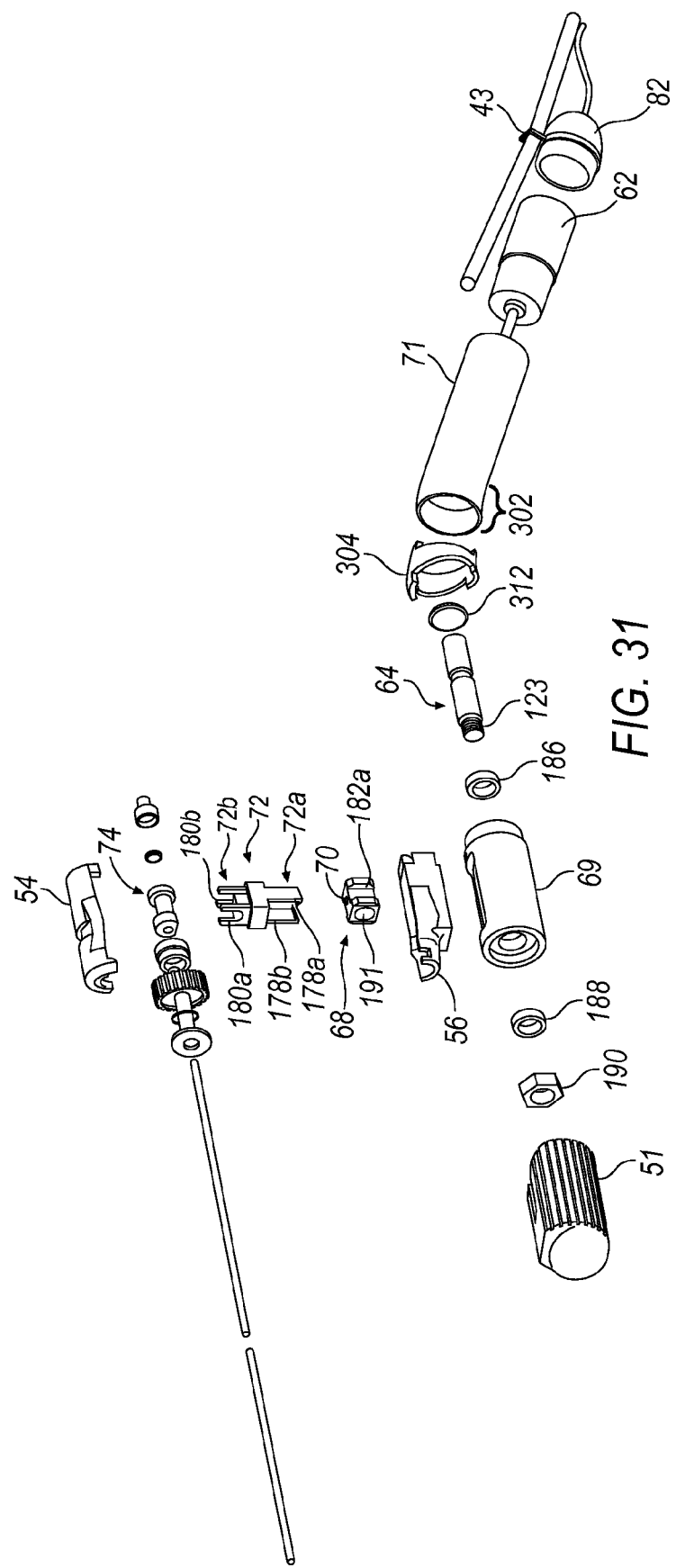
FIG. 31 is an exploded assembly view of the tissue cutting device of FIG. 28.
Figure 33:
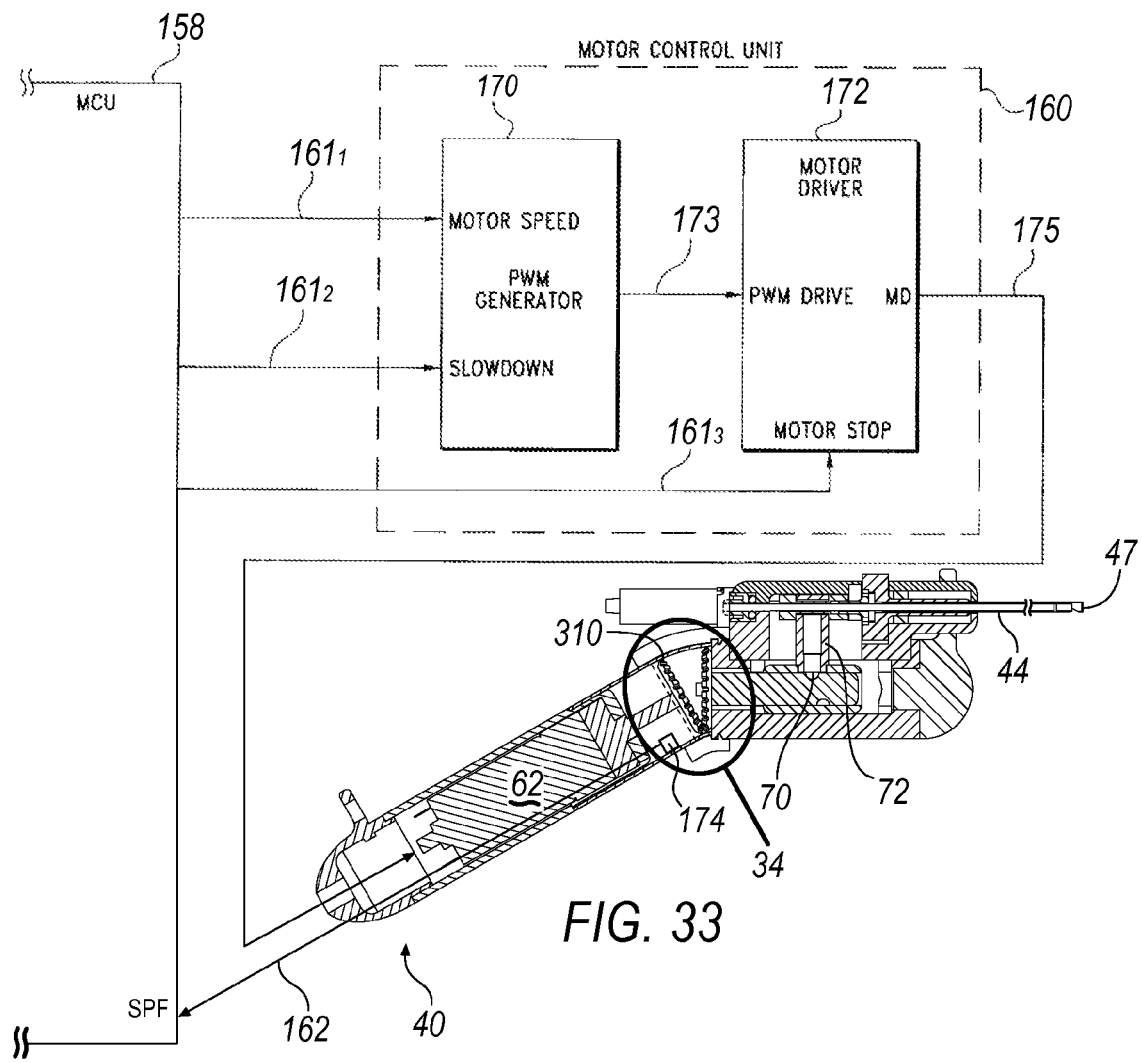
FIG. 33 is diagram of the tissue cutting device of FIG. 28 and the motor control unit of FIG. 22.

Referring to FIG. 28 an alternative embodiment of a tissue cutting device 340 is depicted. Tissue cutting device 340 is configured similarly to and operates in a similar manner to tissue cutting device 40. However, tissue cutting device 340 includes an angled handpiece 342 as well as some modified components which facilitate the use of an angled handpiece. For ease of reference, those components that are the same as those in the embodiment of FIG. 1 are identified by the same reference numerals used previously. Components that are new or which have been modified relative to the embodiment of FIG. 1 have been assigned a "300" series figure number. FIGS. 29 and 30 depict device 340 with inner cannula 76 in a proximal position and a distal position, respectively. FIG. 31 depicts an exploded view of device 340.

In accordance with the embodiment, tissue cutting device 340 includes a handpiece 342 and an outer cannula 44 that is offset from the handpiece 342. Unlike the previous embodiments of a tissue cutting device, handpiece 342 is angled, not straight. Thus, handpiece 342 includes a lower housing 350 which comprises a proximal handpiece section 346 and distal handpiece section 348. Lower housing 350 comprises a proximal-most housing portion 82 (FIGS. 2 and 3) that is connected to a motor housing 71, and a cam housing 69 that is connected to motor housing 71. A front housing section 55 is connected to cam housing 69. Upper housing 52 is also provided and is connected to lower housing distal handpiece section 348. Upper housing 52 is spaced apart from cam 64 in the radial direction of distal handpiece section 348, i.e., in a direction that is perpendicular to inner cannula longitudinal axis $L_1$. A tissue collector 58 may be remotely or directly connected to upper housing 52 as described previously. A rotation dial 60 for rotating the outer cannula 44 with respect to handpiece 42 is also mounted to upper housing 52.

Inner cannula 76 is disposed in outer cannula 44 and reciprocates within outer cannula lumen 110 in the manner described previously. Inner cannula 76 has a longitudinal axis $L_1$ extending along its length through its radial center point. Inner cannula 76 and outer cannula 44 are partially disposed in upper housing 52 and project away from its distal end.

Distal handpiece section 348 has a longitudinal axis $L_2$ extending along its length through the radial center point of cam 64. Inner cannula longitudinal axis $L_1$ is spaced apart from and substantially parallel to distal handpiece section longitudinal axis $L_2$. Proximal handpiece section 346 and distal handpiece section 348 define an angle α (FIGS. 29-30) between proximal handpiece section 346 and distal handpiece section 348. In certain examples, the angled handpiece 342 allows the surgeon to grip tissue cutting device 340 at an orientation that is angled with respect to the direction of surgical entry into the patient. In certain other examples, distal handpiece section 348 is grippable with a single hand, and the angled design provides a clearance between proximal handpiece section 346 and adjacent instruments or devices.

The angle α between distal handpiece section 348 and proximal handpiece section 346 is preferably set to provide a desired degree of manipulability of device 340 while preventing the device 340 from contacting adjacent instruments or devices. The angle α preferably ranges from at least about 90° to less than 180°, more preferably from about 110° to about 160°, even more preferably from at least about 130° to about 150°, still more preferably from at least about 140° to about 160°, and most preferably from about 145° to about 155°.

Proximal handpiece section 346 has a longitudinal axis $L_3$ that extends through its radial centerpoint. As indicated in FIG. 29, axis $L_3$ intersects both axis $L_2$ and axis $L_3$. Proximal handpiece section 346 is spaced apart from inner cannula longitudinal axis $L_1$ in a direction h that is substantially perpendicular to inner cannula longitudinal axis $L_1$. In addition, the spacing between inner cannula longitudinal axis $L_1$ and proximal handpiece section 346 (i.e., the spacing in direction h) increases from the distal end of proximal handpiece section 346 to the proximal end of proximal handpiece section 346.

Distal end 302 (FIGS. 29-30) of proximal handpiece section 346 is preferably curved to facilitate its attachment to the proximal end of distal handpiece section 348. In one example, proximal handpiece section 346 is removably attachable to distal handpiece section 348. In another example, proximal handpiece section 346 and distal handpiece section 348 are configured for a snap-fit connection to one another. One such snap-fit design is illustrated in FIGS. 29, 30, and 31. In accordance with the figures, handpiece 342 includes a collar 304 that is fixedly attached to the curved distal end 302 of proximal handpiece section 346. Collar 304 includes a distal, radially inward projecting ridge 306. Ridge 306 is preferably constructed of a resilient material such as a resilient plastic. The proximal end of distal handpiece section 348 includes a groove or channel 308 into which ridge 306 fits. Thus, collar 304 can be slid over the proximal end of distal handpiece section 348 allowing the ridge 306 to snap into place in groove 308. Connection mechanisms other than ridges and grooves may be used. For example, collar 304 may include a plurality of radially inward facing tabs that engage complementary slots formed in the proximal end of distal handpiece section 348. Proximal handpiece section 346 may be connected to distal handpiece section 348 by other or additional means such as an adhesive or mechanical fasteners as well.

Figure 34:
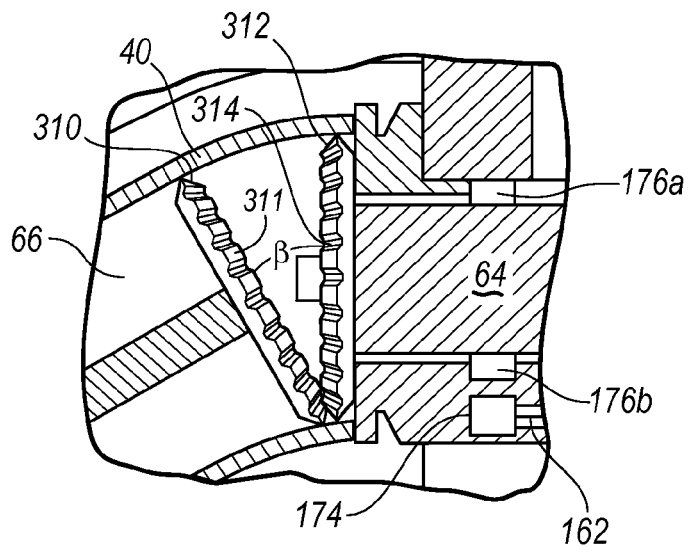
FIG. 34 is a partial cross-sectional view of the tissue cutting device of FIG. 28 depicting motor shaft position sensors for controlling a stop position of an inner cannula.

As with the previous embodiment, motor 62 is operatively connected to cam 64 such that when motor shaft 66 rotates about proximal handpiece section longitudinal axis $L_3$, cam 64 rotates about distal handpiece section longitudinal axis $L_2$. However, in the embodiment of FIGS. 28-34, motor 62 rotates about an axis ($L_3$) that is not collinear with the axis ($L_2$) about which cam 64 rotates. A rotary motion conversion mechanism is preferably provided to convert the rotation of motor 62 about axis $L_3$ to the rotation of cam 64 about axis $L_2$. One such mechanism is depicted in FIGS. 29-30. As shown therein, motor 62 includes a shaft 66 with a drive gear 310 mounted to the distal end of shaft 66. Drive gear 310 engages a driven gear 312 that is mounted on the proximal end of cam 64, as best seen in FIGS. 32A and 32B. In one example, drive gear 310 has teeth 311 (FIG. 34) that intermesh with complementary teeth 314 formed on driven gear 312. In the implementation depicted in FIGS. 29-34, both drive gear 310 and driven gear 312 are beveled gears that engage one another to define an angle β between drive gear 310 and driven gear 312. The angle β preferably ranges from greater than 0° to about 900, more preferably ranges from about 20° to about 70°, even more preferably ranges from about 30° to about 600, and still more preferably ranges from about 40° to about 50°.

Tissue cutting device 340 operates identically to device 40 in all respects except for the manner in which the rotation of motor 62 is converted to the rotation of cam 64. Thus, when motor 62 is energized, it rotates, causing shaft 66 and drive gear 310 to rotate about proximal handpiece section longitudinal axis $L_3$. The engagement of drive gear 310 and driven gear 312 causes driven gear 312 to rotate about distal handpiece section longitudinal axis $L_2$. Because driven gear 312 is mounted on cam 64, as driven gear 312 rotates, cam 64 begins to rotate about distal handpiece section longitudinal axis $L_2$. The ball bearing (not shown) disposed in cam follower hole 70 traverses cam groove 65 as cam 64 rotates, causing cam follower 68 to reciprocate from the proximal position of FIG. 29 to the distal position of FIG. 30. As a result, cam transfer 72, cannula transfer 74 and inner cannula 76 translate between their respective proximal positions of FIG. 29 and their respective distal positions of FIG. 30 when motor 62 and cam 64 rotate.

Motor 62 is preferably selected to have a rotational speed that allows inner cannula 76 to reciprocate from the position of FIG. 29 to the position of FIG. 30 and back to the position of FIG. 29 at a rate of at least about 1,000 reciprocations/minute. Reciprocation rates of at least about 1,200 reciprocations/minute are more preferred, and reciprocation rates of at least about 1,500 reciprocations/minute are even more preferred. Reciprocation rates of less than about 2,500 reciprocations/minute are preferred. Reciprocation rates of less than about 2,000 are more preferred, and reciprocation rates of less than about 1,800 reciprocations/minute are even more preferred. As best seen in FIG. 14, the rates of reciprocation of device 40 allow tissue to be severed into "snippets" 112 which are relatively smaller than "slug" tissue samples obtained by many prior devices. As the reciprocation continues, a continuum of severed tissue snippets 112 is obtained.

As mentioned previously, angled handpiece 342 allows a surgeon to grip device 340 with a single hand while keeping the hand out of a line of sight along inner cannula longitudinal axis $L_1$. In accordance with one method of use, device 340 is used to perform a tissue cutting procedure involving the cutting of a neurological target tissue. In one example, the target tissue is brain tissue, and in another example the target tissue is spinal tissue, for example, the tissue of an intervertebral disk. In certain exemplary methods, the tissue specimen being cut is a tumor or a lesion.

In accordance with the method, it is first determined whether the cutting operation will be a debulking operation or a fine shaving operation or a cutting operation that is somewhere in between a debulking and fine shaving operation. A given surgical procedure may also involve various combinations of these operations. A surgical access path is then created to the tissue sample of interest. In one embodiment, the surgical path is created and/or the target tissue is accessed using an "open" procedure in which the target tissue is open to the atmosphere (e.g., a full open craniotomy). In another embodiment, the surgical path is created and/or the target tissue is accessed using a "closed" procedure in which the target tissue is sealed from the atmosphere.

At this point, the distal end 79 of inner cannula 76 is located proximally of outer cannula opening 49 due to the use of an inner cannula stop position control of the type described previously. The maximum vacuum level to be applied to device 40 is then set using panel controls 138. Generally, higher vacuum levels will be used for debulking procedures than for fine shaving procedures as higher vacuum levels will tend to draw relatively larger sections of tissue into outer cannula opening 49. In one embodiment, the panel control 138 is a knob on console 134 that is rotated to set the desired maximum vacuum level.

Figure 36:
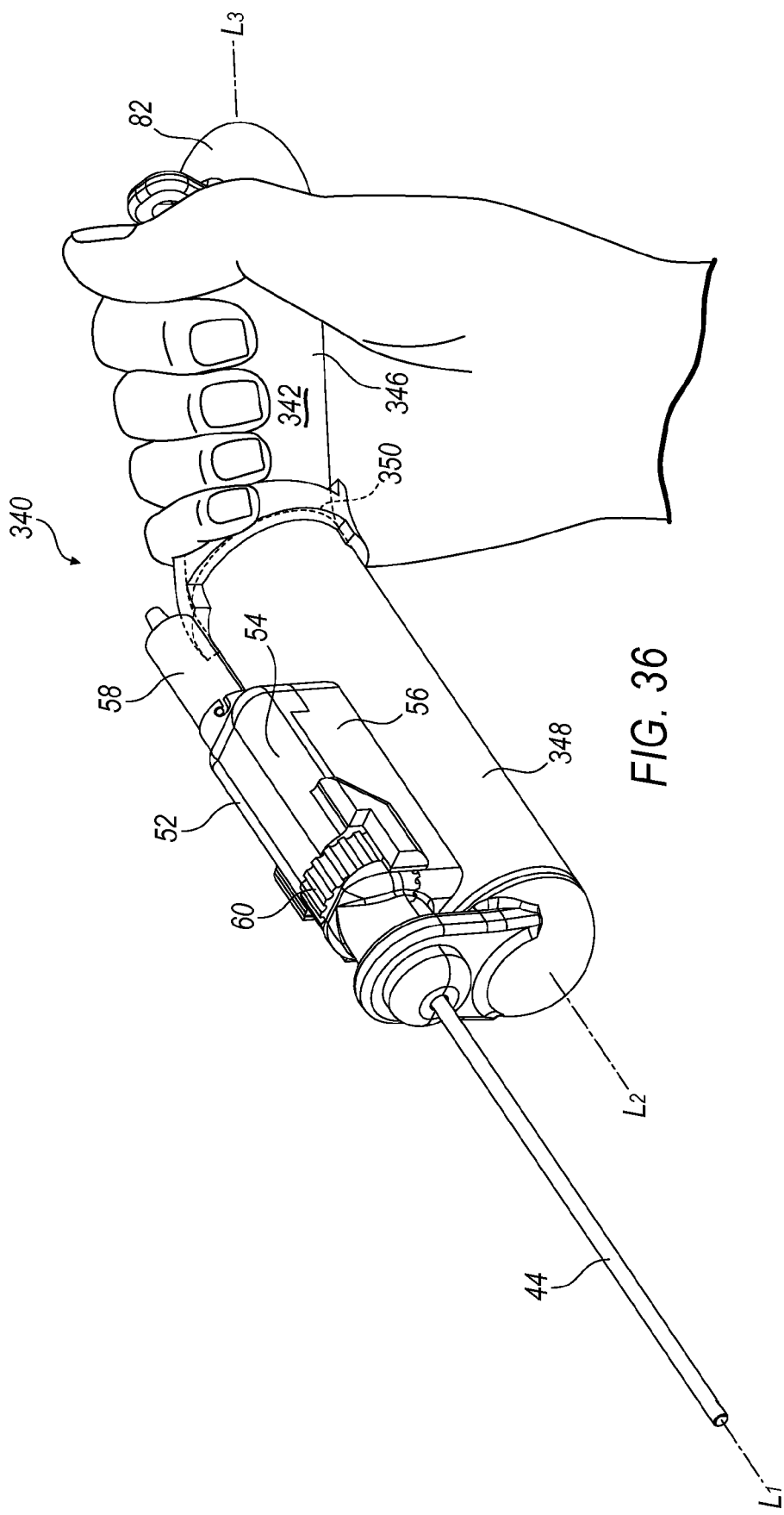
FIG. 36 depicts a first method of gripping the tissue cutting device of FIG. 28 in a single hand.
Figure 37:
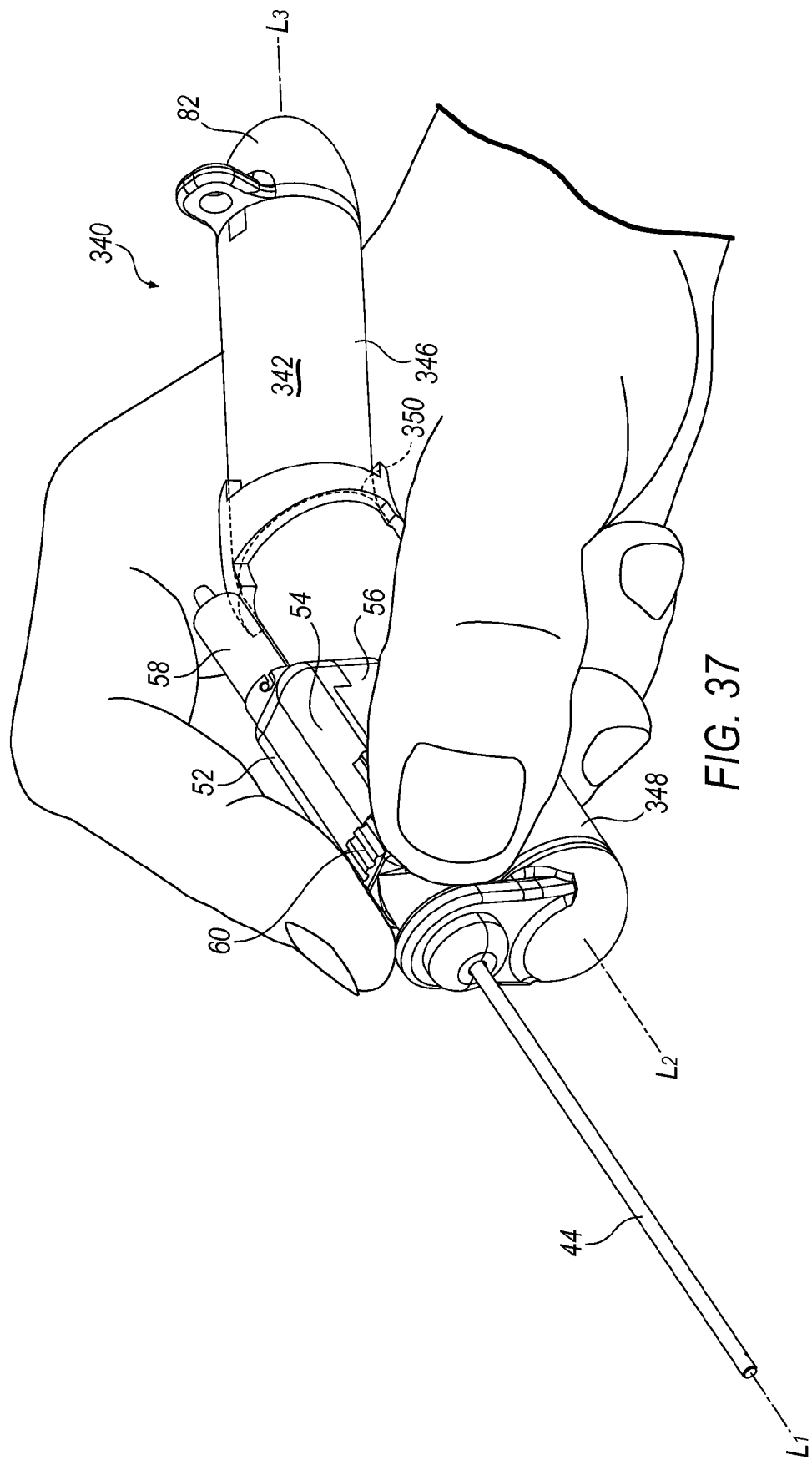
FIG. 37 depicts a second method of gripping the tissue cutting device of FIG. 28 in a single hand.
Figure 38:
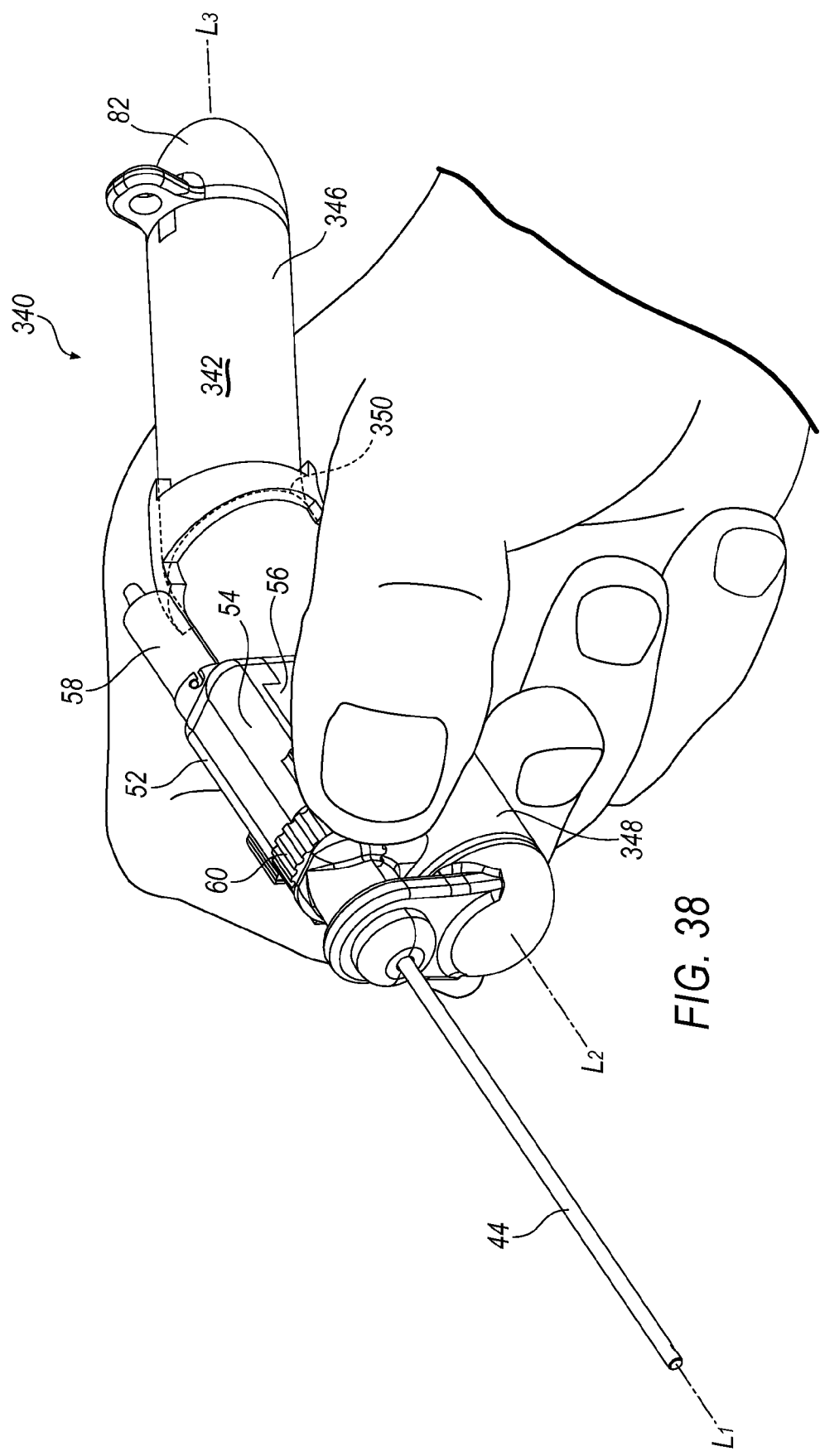
FIG. 38 depicts a third method of gripping the tissue cutting device of FIG. 28 in a single hand.

In one arrangement, device 340 is configured to be gripped with a single hand during a tissue cutting procedure. The surgeon may grip angled handpiece 342 in a number of ways. In one example, depicted in FIG. 36, the surgeon grips proximal handpiece section 346 in one hand with the thumb placed adjacent proximal-most housing portion 82 and the fourth finger placed adjacent distal handpiece section 348. Another grip is depicted in FIG. 37. In FIG. 37, distal housing section 348 is gripped with the fingers of one hand. As shown in the figure, the thumb is placed on one side of upper housing 52 and the index finger is placed on an upper surface of upper housing 52. Proximal handpiece section 346 rests between the base of the thumb and index finger. The index finger may be placed on rotation dial 60 to facilitate the rotation of outer cannula 44 and inner cannula 76. In yet another example, shown in FIG. 38, distal housing section 348 is again gripped with the fingers of one hand. However, the thumb is placed on one side of upper housing 52 and the index finger is placed on the other side of upper housing 52, with the proximal handpiece section resting between the base of the thumb and index finger.

Figure 35A:
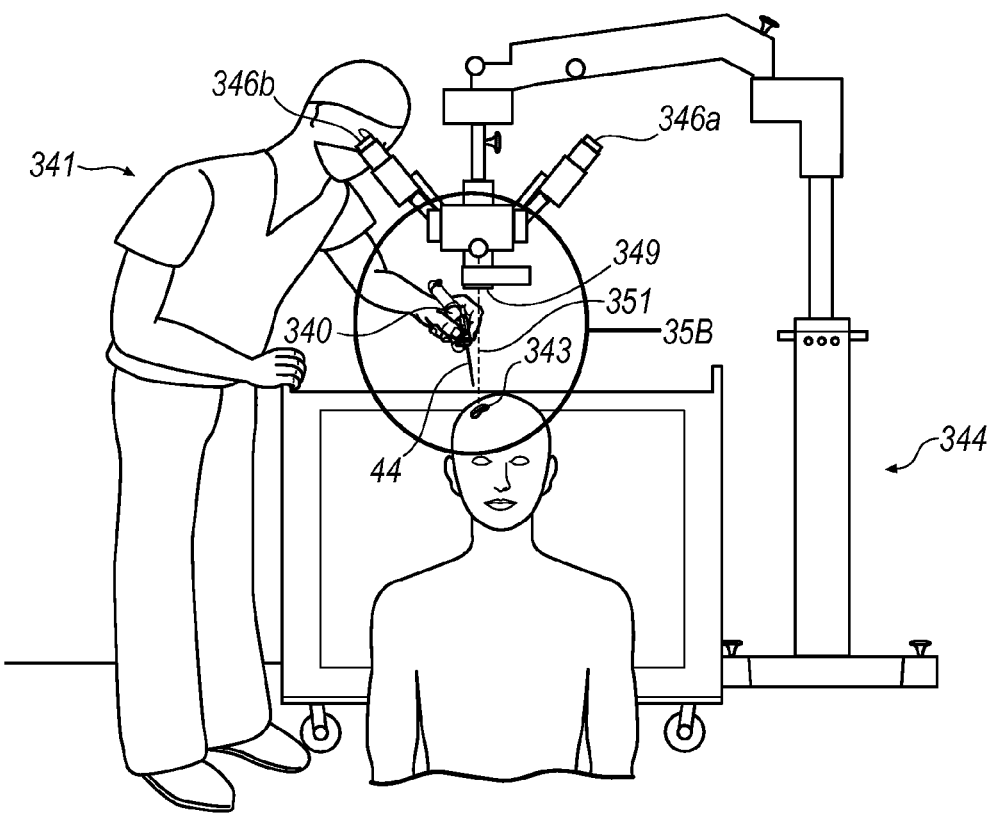
FIG. 35A depicts a method of using the tissue cutting device of FIG. 28 to perform a microscope assisted neurosurgical procedure.
Figure 35B:
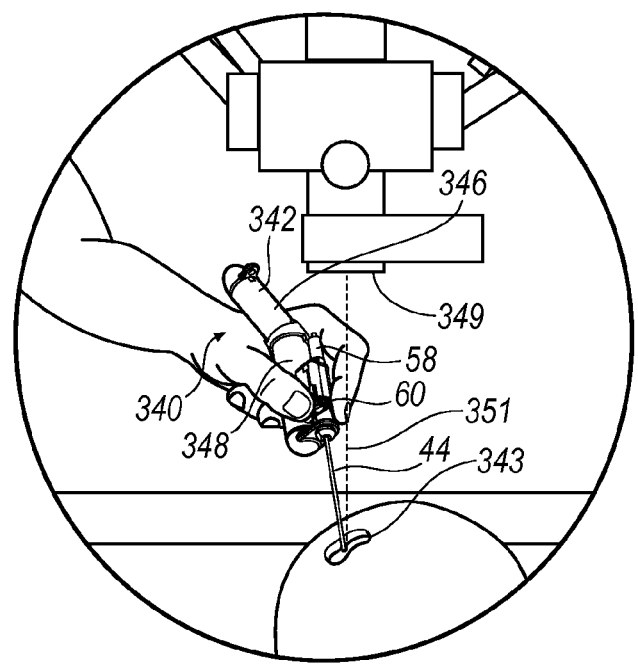
FIG. 35B is a detail view of a portion of FIG. 35B.

In one example, the surgeon may align outer cannula 44 with the target tissue by viewing the proximal portion of the upper housing 52 along a line of sight that is substantially collinear with inner cannula longitudinal axis $L_1$ and aligning axis $L_1$ with the target tissue. In certain cases, the handpiece angle α will preferably be large enough to prevent device 340 from bumping adjacent instruments. In one preferred embodiment depicted in FIG. 35A, tissue cutting device 340 is used to perform an open procedure using a microscope 344. In accordance with the embodiment, the lens 349 of the microscope 344 is aligned with the target tissue 343 so that the target tissue is in a line of sight 351 of the microscope's field of view. The outer cannula 44 is then positioned in the microscope's field of view between the lens 349 and the target tissue 343. The surgeon 341 views the tissue cutting device 340 and inserts outer cannula 44 to a location proximate the target tissue 343 and cuts the target tissue 343 in the manner described previously. In one example, the entire distal handpiece section 348 is placed in the microscope's field of view between the microscope lens 349 and the target tissue 343 along a direction parallel to line of sight 351. The surgeon 341 then inserts the outer cannula 44 to the desired location proximate the target tissue 343 to begin cutting. In one exemplary method, best seen in FIG. 35B, the surgeon 341 grasps the distal handpiece section 348 with the fingers of one hand while inserting the outer cannula 44 into the patient, and the proximal handpiece section 346 bends away from microscope 344. Thus, upper housing 52 and outer cannula 44 are positioned between distal handpiece section 348 and microscope line of sight 351. In addition, proximal handpiece portion 346 is not disposed between lens 349 and target tissue 343 in a direction along line of sight 351. Instead, proximal handpiece section 346 extends above the vertical location of lens 349. This configuration allows lens 349 to be placed more closely to target tissue 343 than would otherwise be possible if proximal handpiece section 346 were collinearly aligned with distal handpiece section 348. In the example depicted in FIG. 35B, tissue cutting device 340 is positioned such that a distance is defined between lens 349 and the proximal-most end of distal handpiece section 348, which is less than the length of proximal handpiece section 346 (i.e., the length from proximal-most housing section 82 to the vertex of the angle β that is defined between drive gear 310 and driven gear 312). Depending on the hand and the surgeon's orientation with respect to the target tissue 343, the surgeon may then rotate dial 60 to rotate outer cannula 44 about its own longitudinal axis as mentioned previously. Motor 62 may then be activated to reciprocate the inner cannula 76 as described previously (and as further illustrated in FIG. 33) to cut the target tissue, and the level of vacuum in inner cannula lumen 78 may be adjusted to achieve the desired degree of traction based on considerations such as whether a debulking or fine shaving operation is desired.

It will be appreciated that the tissue cutting devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed as new and desired to be protected by Letters Patent of the United States is:

1. A tissue removal device, comprising:
   a handpiece having a proximal section and a distal section, wherein a motor having a motor longitudinal axis is disposed in the proximal section, the distal handpiece section having a distal handpiece section longitudinal axis, wherein the proximal section and the motor longitudinal axis are angled with respect to the distal section longitudinal axis;
   an outer cannula having an outer cannula lumen, a proximal end, a distal end, and an outer cannula opening adjacent the distal end, wherein the opening adjacent the distal end defines a cutting edge for severing tissue;
   an inner cannula disposed in the outer cannula lumen and reciprocable within the outer cannula lumen, the inner cannula having an inner cannula longitudinal axis, an inner cannula lumen, a proximal end, an open distal end, and a cutting edge at the distal end, wherein when the motor rotates, the inner cannula reciprocates within the outer cannula lumen;
   a tissue collector in fluid communication with the inner cannula lumen;
   a cam disposed in the distal handpiece section, wherein the motor is operatively connected to the cam such that when the motor rotates, the cam rotates about a cam axis, and the inner cannula reciprocates within the outer cannula lumen, the cam defining a cam groove, the cam groove angled with respect to the cam axis; and
   a cam transfer spacing the inner cannula laterally from the distal housing longitudinal axis, wherein the cam transfer extends between a first end that engages the cam and a second end that engages the inner cannula, such that when the cam rotates, the cam transfer follows the cam groove such that the cam transfer reciprocates in a direction that is substantially parallel to the inner cannula longitudinal axis.

2. The tissue removal device of claim 1, wherein the handpiece has an angle between the proximal section and the distal section, and the angle is from about 90° to less than 180°.

3. The tissue removal device of claim 1, wherein the angle is from about 90° to about 150°.

4. The tissue removal device of claim 1, wherein the outer cannula is located distally from the proximal handpiece section.

5. The tissue removal device of claim 1, wherein the inner cannula is located distally from the proximal handpiece section.

6. The tissue removal device of claim 1, wherein the motor has a rotating shaft, and the rotating shaft is spaced apart from the inner cannula longitudinal axis in a direction that is substantially perpendicular to the inner cannula longitudinal axis.

7. The tissue removal device of claim 1, further comprising an upper housing connected to the distal handpiece section and spaced apart from the distal handpiece section longitudinal axis, wherein a portion of the outer cannula is disposed in the upper housing, and the distal end of the outer cannula projects away from the upper housing.

8. The tissue removal device of claim 1, wherein the cam has a longitudinal axis, the motor has a longitudinal axis, and the cam longitudinal axis intersects the motor longitudinal axis.

9. The tissue removal device of claim 1, wherein the motor is connected to a drive gear, the cam is connected to a driven gear, and the drive gear engages the driven gear.

10. The tissue removal device of claim 9, wherein the drive gear engages the driven gear such that an angle is defined between the drive gear and the driven gear.

11. The tissue removal device of claim 10, wherein the angle is from greater than 0° to about 90°.

12. The tissue removal device of claim 11, wherein the angle is from about 20° to about 70°.

13. The tissue removal device of claim 1, wherein the outer cannula has a longitudinal axis that is spaced apart from and substantially parallel to the distal handpiece section longitudinal axis.

14. The tissue removal device of claim 1, wherein the proximal handpiece section is spaced apart from the inner cannula longitudinal axis in a direction that is substantially perpendicular to the inner cannula longitudinal axis.

15. A tissue removal system comprising the tissue removal device of claim 1 and a vacuum generator in fluid communication with the inner cannula lumen.

16. The tissue removal device of claim 1, wherein the outer cannula is rotatable with respect to the handpiece, and when the outer cannula is rotated with respect to the handpiece, the inner cannula rotates with respect to the handpiece to maintain a fixed circumferential orientation between the outer cannula and the inner cannula.

17. The tissue removal device of claim 1, wherein the cam axis his a cam longitudinal axis, and wherein the cam longitudinal axis is substantially parallel to the distal housing longitudinal axis and the inner cannula longitudinal axis, and wherein the cam longitudinal axis is angled with respect to the motor longitudinal axis.

18. The tissue removal device of claim 1, wherein the inner cannula comprises a living hinge, a cutting section, and a body section, with the hinge being located between the cutting section and the body section, wherein the cutting section is pivotable when the inner cannula reciprocates within the outer cannula lumen.

19. The tissue removal device of claim 1, wherein the cam transfer first end is engaged with the cam groove such that rotational motion of the cam about the cam axis reciprocates the cam transfer.

20. The tissue removal device of claim 19, wherein the cam transfer first end is engaged with the cam groove with a ball bearing received by the cam transfer first end and the cam groove.

21. A method of performing a neurosurgical procedure, comprising:
   providing a tissue removal device comprising:
      a handpiece having a proximal section and a distal section, wherein a motor having a motor longitudinal axis is disposed in the proximal section, the distal handpiece section having a distal handpiece section longitudinal axis, wherein the proximal section and the motor longitudinal axis are angled with respect to the distal section longitudinal axis,
      an outer cannula having an outer cannula lumen, a proximal end, a distal end, and an outer cannula opening adjacent the distal end, wherein the opening defines a cutting edge for severing tissue,
      an inner cannula disposed in the outer cannula lumen and reciprocable within the outer cannula lumen, the inner cannula having an inner cannula longitudinal axis, an inner cannula lumen, a proximal end, a distal end, and a cutting edge at the distal end, wherein when the motor rotates, the inner cannula reciprocates within the outer cannula lumen;

a cam disposed in the distal handpiece section, wherein the motor is operatively connected to the cam such that when the motor rotates, the cam rotates about a cam axis, and the inner cannula reciprocates within the outer cannula lumen, the cam defining a cam groove, the cam groove angled with respect to the cam axis; and a cam transfer spacing the inner cannula laterally from the distal housing longitudinal axis, wherein the cam transfer extends between a first end that engages the cam and a second end that engages the inner cannula, such that when the cam rotates, the cam transfer follows the cam groove such that the cam transfer reciprocates in a direction that is substantially parallel to the inner cannula longitudinal axis;

gripping the handpiece with the fingers of one hand;

inserting the outer cannula into a patient proximate target tissue associated with the patient's neurological system; and reciprocating the inner cannula within the outer cannula lumen between a proximal position and a distal position, such that when the inner cannula is in the proximal position, the target tissue is received in the outer cannula opening, and when the inner cannula is in the distal position, the cutting section pivots and the received target tissue is severed from surrounding tissue.

22. The method of claim 21, further comprising providing a microscope having a lens, and positioning the outer cannula between the lens and the target tissue.

23. The method of claim 21, further comprising providing a microscope having a lens and positioning the distal handpiece section between the lens and the target tissue.

24. The method of claim 23, wherein the lens and the distal handpiece section define a distance between the lens and the distal handpiece section, the proximal handpiece section has a length, and the length of the proximal handpiece section is greater than the distance.

25. The method of claim 21, wherein the handpiece has an angle between the proximal handpiece section and the distal handpiece section, and the angle is from about 90° to less than 180°.

26. The method of claim 25, wherein the angle is from about 110° to about 160°.

27. The method of claim 21, further comprising rotating the outer cannula with respect to the handpiece to align the outer cannula opening with the target tissue.

28. The method of claim 27, wherein the step of rotating the outer cannula with respect to the handpiece comprises simultaneously rotating the inner cannula with respect to the handpiece to maintain a fixed circumferential orientation between the inner cannula and the outer cannula opening.

29. The method of claim 21, wherein the target tissue is spinal tissue.

30. The method of claim 21, wherein the target tissue is brain tissue.

31. The method of claim 21, wherein the target tissue comprises a tumor.

32. The method of claim 21, wherein the target tissue comprises a lesion.

33. The method of claim 21, further comprising aspirating severed tissue samples from the distal end of the inner cannula to the proximal end of the inner cannula.

34. The tissue removal device of claim 17, wherein the cam longitudinal axis is spaced laterally from the inner cannula longitudinal axis.

35. The method of claim 21, wherein the cam axis is a cam longitudinal axis, and wherein the cam longitudinal axis is substantially parallel to the distal housing longitudinal axis and the inner cannula longitudinal axis, and wherein the cam longitudinal axis is angled with respect to the motor longitudinal axis.

36. The method of claim 21, wherein the inner cannula comprises a living hinge, a cutting section, and a body section, with the hinge being located between the cutting section and the body section, wherein the cutting section is pivotable when the inner cannula reciprocates within the outer cannula lumen.

37. The method of claim 21, wherein the cam transfer first end is engaged with the cam groove such that rotational motion of the cam about the cam axis reciprocates the cam transfer.

38. The method of claim 37, wherein the cam transfer first end is engaged with the cam groove with a ball bearing received by the cam transfer first end and the cam groove.

* * * * *

UNITED STATES PATENT AND TRADEMARK OFFICE
CERTIFICATE OF CORRECTION

Page 1 of 1

PATENT NO.        : 8,702,738 B2
APPLICATION NO.   : 12/391579
DATED             : April 22, 2014
INVENTOR(S)       : Joseph L. Mark It is certified that error appears in the above-identified patent and that said Letters Patent is hereby corrected as shown below:

In the Claims

Column 26, line 33, claim 17:

Change [his] to -is-

Signed and Sealed this
Twenty-fourth Day of June, 2014

Michelle K. Lee
*Deputy Director of the United States Patent and Trademark Office*